(12) United States Patent
Wolfertz et al.

(10) Patent No.: US 10,959,878 B2
(45) Date of Patent: Mar. 30, 2021

(54) MEDICAL CATHETER FOR HYPOTHERMIC TREATMENT, TREATMENT SYSTEM WITH SUCH A CATHETER, AND PRODUCTION METHOD

(71) Applicant: ACANDIS GMBH & CO. KG, Pfinztal (DE)

(72) Inventors: Julia Wolfertz, Bad Homburg (DE); Giorgio Cattaneo, Karlsruhe (DE); Michael Büchert, Bretten (DE)

(73) Assignee: ACANDIS GMBH, Pforzheim (DE)

( * ) Notice: Subject to any disclaimer, the term of this patent is extended or adjusted under 35 U.S.C. 154(b) by 941 days.

(21) Appl. No.: 14/891,142

(22) PCT Filed: May 14, 2014

(86) PCT No.: PCT/EP2014/059837
§ 371 (c)(1),
(2) Date: Nov. 13, 2015

(87) PCT Pub. No.: WO2014/184238
PCT Pub. Date: Nov. 20, 2014

(65) Prior Publication Data
US 2016/0095744 A1    Apr. 7, 2016

(30) Foreign Application Priority Data

May 14, 2013 (DE) .............. 102013104948

(51) Int. Cl.
*A61F 7/12*     (2006.01)
*A61B 18/02*   (2006.01)
(Continued)

(52) U.S. Cl.
CPC .............. *A61F 7/12* (2013.01); *A61B 18/02* (2013.01); *A61M 25/0009* (2013.01);
(Continued)

(58) Field of Classification Search
CPC .............. A61F 7/12; A61F 2007/126; A61F 2007/0098; A61F 2007/0054;
(Continued)

(56) References Cited

U.S. PATENT DOCUMENTS 4,563,180 A    1/1986  Jervis
5,634,928 A *  6/1997  Fischell .............. A61F 2/95
                                                    606/194
(Continued)

FOREIGN PATENT DOCUMENTS

EP    0729766    9/1996
EP    1709922    10/2006

OTHER PUBLICATIONS

Office Action from German Patent Office dated Apr. 9, 2014, partial machine translation attached.
(Continued)

*Primary Examiner* — Kaitlyn E Smith
*Assistant Examiner* — Yasamin Ekrami
(74) *Attorney, Agent, or Firm* — Hassan Abbas Shakir; Shakir Law PLLC

(57) ABSTRACT

A medical catheter for hypothermic treatment with a catheter tube has at least one through-channel and at least two temperature control channels, at least one heat exchange element, in particular an expandable balloon, which is arranged in a distal catheter portion of the catheter tube and is fluidically connected to the temperature control channels in such a way that a temperature control circuit is formed. The catheter tube has a smaller external diameter in the distal catheter portion than in a proximal catheter portion.

22 Claims, 8 Drawing Sheets

(51) Int. Cl.
*A61M 25/00* (2006.01)
*A61M 25/10* (2013.01)
*A61F 7/00* (2006.01)
*A61M 25/01* (2006.01)
*A61B 18/00* (2006.01)

(52) U.S. Cl.
CPC .... *A61M 25/0021* (2013.01); *A61M 25/0026* (2013.01); *A61M 25/0045* (2013.01); *A61M 25/0054* (2013.01); *A61M 25/1036* (2013.01); *A61B 2018/0022* (2013.01); *A61B 2018/0212* (2013.01); *A61F 2007/0054* (2013.01); *A61F 2007/0091* (2013.01); *A61F 2007/0098* (2013.01); *A61F 2007/126* (2013.01); *A61M 25/0023* (2013.01); *A61M 25/0032* (2013.01); *A61M 25/0082* (2013.01); *A61M 25/0108* (2013.01); *A61M 25/10* (2013.01); *A61M 25/1011* (2013.01); *A61M 2025/0008* (2013.01)

(58) Field of Classification Search
CPC ....... A61F 2007/0091; A61M 25/0009; A61M 25/0021; A61M 25/1036; A61M 25/0026; A61M 25/0045; A61M 25/0054; A61M 25/10; A61M 25/0032; A61M 25/1011; A61M 25/0023; A61M 25/0082; A61B 2018/0022; A61B 2018/0212
See application file for complete search history.

(56) References Cited

U.S. PATENT DOCUMENTS

| | | | | |
|---|---|---|---|---|
| 6,024,722 | A * | 2/2000 | Rau | A61M 25/0045 604/524 |
| 6,126,684 | A * | 10/2000 | Gobin | A61F 7/12 604/113 |
| 6,338,727 | B1 * | 1/2002 | Noda | A61F 7/12 604/113 |
| 2001/0029394 | A1 * | 10/2001 | Dobak, III | A61F 7/12 607/105 |
| 2002/0045892 | A1 | 4/2002 | Kramer | |
| 2002/0082556 | A1 | 6/2002 | Cioanta | |
| 2003/0014095 | A1 * | 1/2003 | Kramer | A61B 18/02 607/106 |
| 2004/0220647 | A1 * | 11/2004 | Noda | A61F 7/12 607/105 |
| 2005/0119682 | A1 * | 6/2005 | Nguyen | A61B 17/12022 606/194 |
| 2006/0058859 | A1 * | 3/2006 | Merrill | A61F 7/12 607/105 |
| 2007/0005092 | A1 | 1/2007 | Godin | |
| 2010/0217304 | A1 * | 8/2010 | Angel | A61F 2/013 606/200 |
| 2010/0234838 | A1 | 9/2010 | Watson | |
| 2012/0041419 | A1 | 2/2012 | Blanchard | |
| 2012/0143131 | A1 | 6/2012 | Tun | |
| 2012/0150107 | A1 * | 6/2012 | Cheung | A61B 5/6853 604/96.01 |
| 2012/0197285 | A1 * | 8/2012 | Martin | A61B 17/221 606/200 |

OTHER PUBLICATIONS

International Search Report with written opinion dated Aug. 5, 2014, search report in English is appended to WO publication of PCT/EP2014/059837, partial machine translation of written opinion provided.

\* cited by examiner

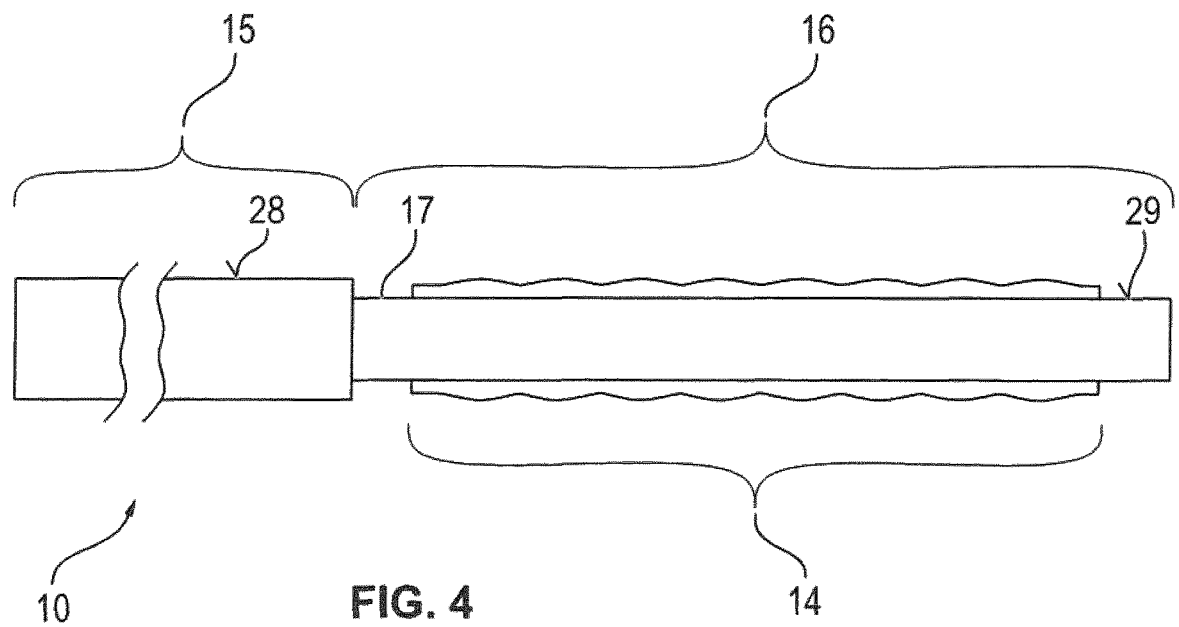
FIG. 4
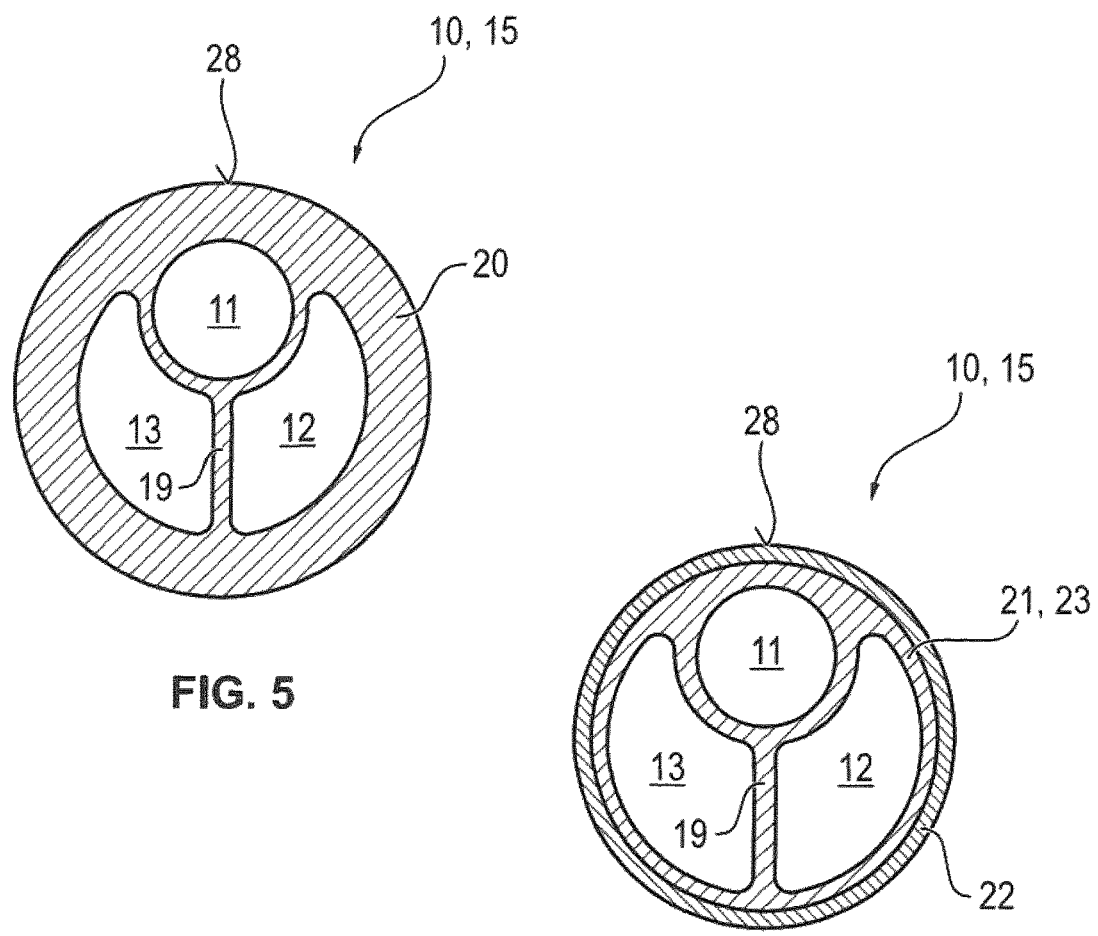
FIG. 5
FIG. 6

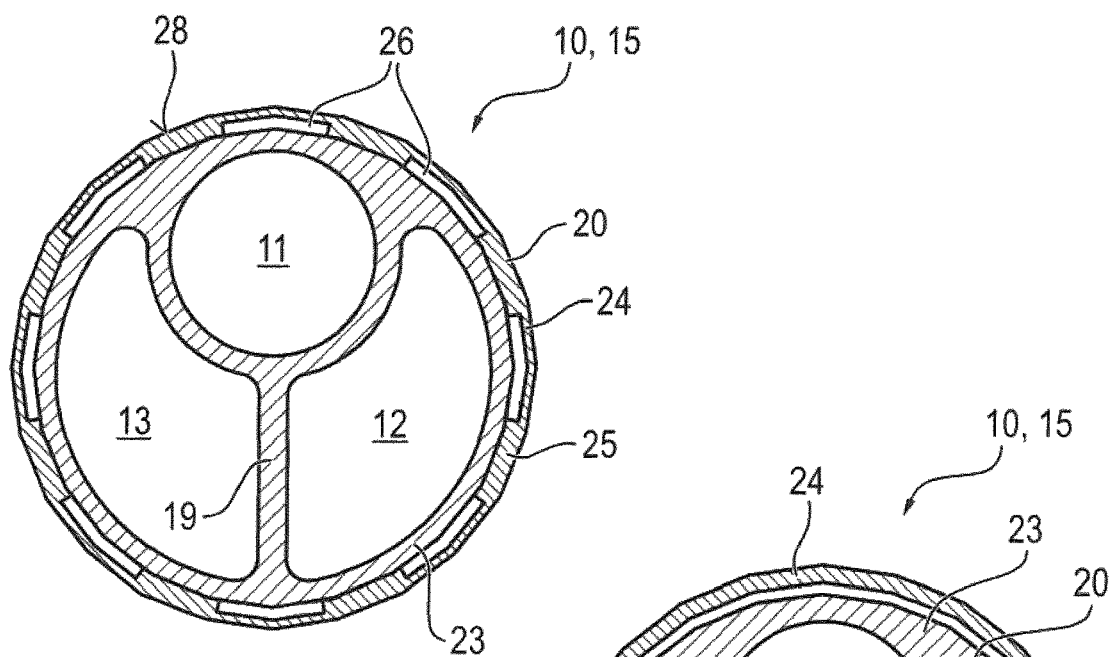
FIG. 7
FIG. 8
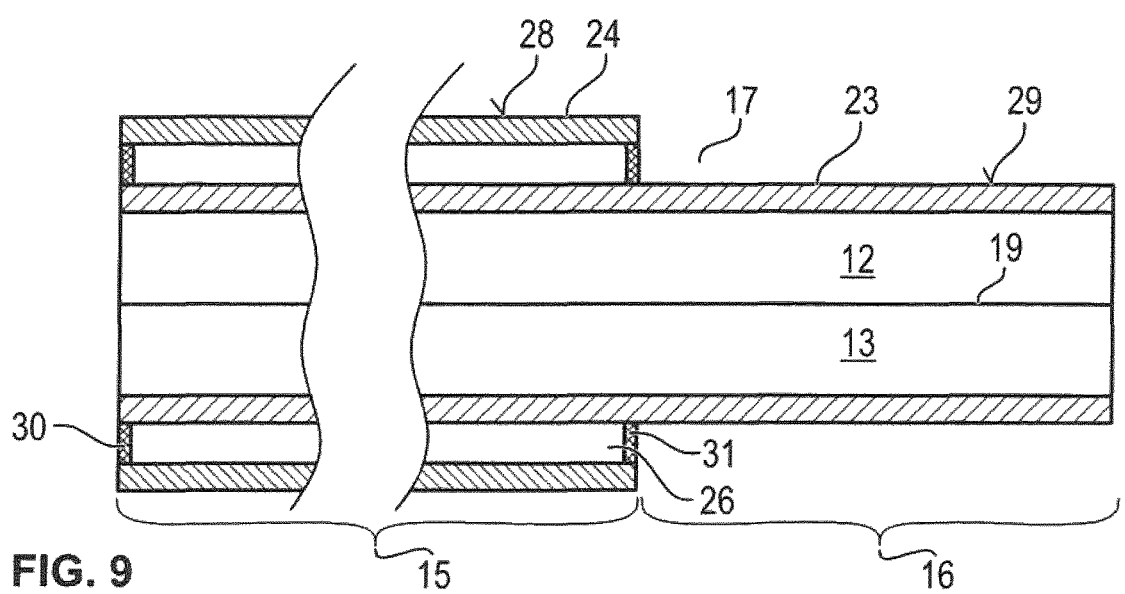
FIG. 9

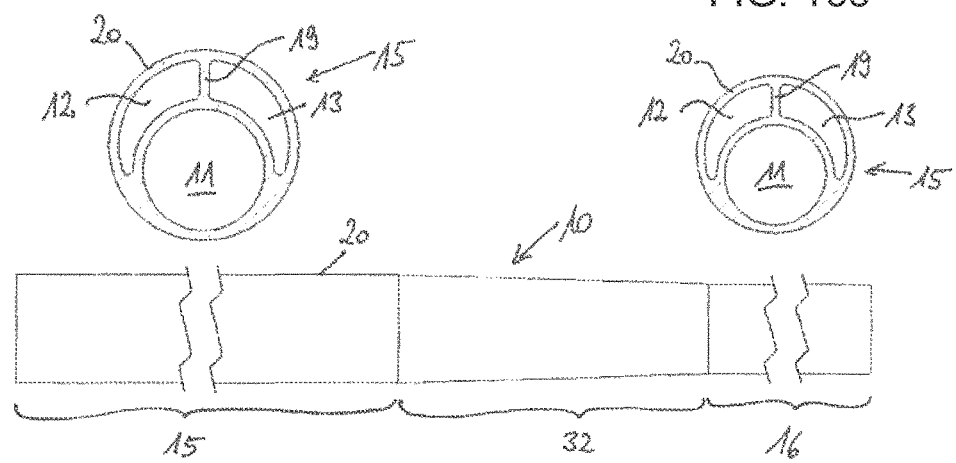
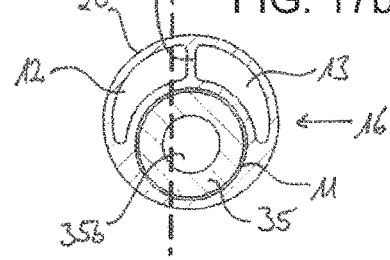
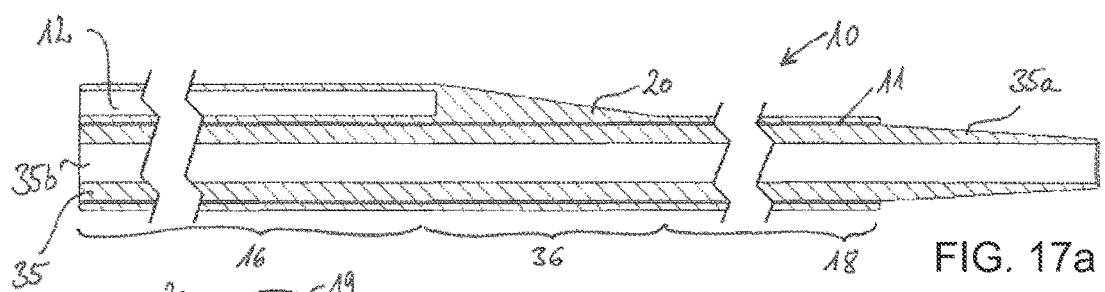
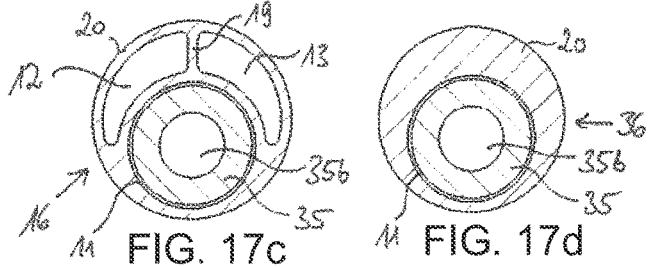

MEDICAL CATHETER FOR HYPOTHERMIC TREATMENT, TREATMENT SYSTEM WITH SUCH A CATHETER, AND PRODUCTION METHOD

BACKGROUND OF THE INVENTION

1. Field of the Invention

The invention relates to a medical catheter for hypothermic treatment. The invention also relates to a treatment system with such a catheter and to a production method.

2. Discussion of the Related Art

A catheter of the type mentioned in the introduction is known, for example, from US 2002/0082556 A1.

Therapeutic hypothermia is used in particular to cool blood in the region of the carotid artery or other cerebral blood vessels. For use of therapeutic hypothermia in cerebral blood vessels, some challenges have to be overcome. On the one hand the blood vessels in the cerebral region are relatively small and on the other hand they are often highly tortuous, and so stringent requirements are imposed on the flexibility of the catheter. At the same time, it is expedient for efficient, local cooling when the catheter has an insulating effect, in order to ensure that cooling takes place mainly at one point of the catheter, especially at the catheter tip. The efficiency of catheter-based hypothermia is also increased with the volume flow of the cooling fluid being passed through the lumens of the catheter. Therefore it is also desirable to make the cross-sectional diameter of the cooling lumens as large as possible. Nevertheless, the catheter should have a small outside diameter and good bending flexibility in order that peripheral blood vessels can also be reached easily.

Usually a sheath having a limited inside diameter is used to advance the catheter. In known hypothermia catheters, such as, for example, the catheter from US 2002/0082556 A1 mentioned in the introduction, a balloon is used as the heat-exchanger element. In compressed condition, the balloon has an outside diameter larger than the catheter tube diameter in a proximal portion of the catheter tube. Thus the remaining annular space between the proximal catheter portion and the sheath is not used.

SUMMARY OF THE INVENTION

The object of the invention is to specify a medical catheter for hypothermic treatment that can be fed easily into small tortuous vessels and has an expedient insulating effect. It is further intended that the space available in a sheath can be used optimally. A further object of the invention is to specify a treatment system with such a catheter as well as a production method.

Thus the invention is based on the idea of specifying a medical catheter for hypothermic treatment with a catheter tube that has at least one through-lumen and at least two temperature-regulating lumens. The catheter has at least one heat-exchanger element, especially an expandable balloon, which is disposed in a distal catheter portion of the catheter tube. The heat-exchanger element is in fluid communication with the temperature-regulating lumens, so that a temperature-regulating circuit is formed. According to the invention, the catheter tube has a smaller outside diameter in the distal catheter portion than in a proximal catheter portion.

By the fact that the catheter tube has a smaller outside diameter in the distal catheter portion than in the proximal catheter portion, the space available in a sheath is used to good purpose. In the remaining receiving space, the heat-exchanger element can be disposed between the outside diameter of the proximal catheter portion and the outside diameter of the distal catheter portion, without increasing the outside diameter of the catheter tube on the whole. Thus the space available in a sheath is filled optimally.

In principle, the catheter may also be used without a sheath. In this respect, the catheter itself may assume the function of a sheath or act as such. In the scope of the present application, this embodiment is referred to as the sheath variant. Accordingly, the catheter may be introduced into a blood vessel directly through the vessel wall. The inventive construction of the catheter also has advantages in this case. Especially by virtue of the reduced cross-sectional diameter in the distal catheter portion in which the heat-exchanger element is also disposed, it is ensured that the overall diameter of the catheter, i.e. of the catheter tube including the heat exchanger element, exhibits hardly any or zero traumatic effects while being advanced through the vessel wall. In the sheath variant (wherein the catheter additionally assumes the function of a sheath), traumatization of tissue is consequently reduced during introduction of the catheter.

In other words, the catheter or the catheter tube is itself able, in special embodiments of the invention, to form a sheath, through which a catheter, especially a guide catheter, can in turn be advanced. A distal diametric reduction of the shaft is also provided in this case, so that, after at least one expandable heat-exchanger element, especially a balloon, has been mounted, the overall outside diameters in the compressed condition of the heat-exchanger element are approximately identical distally and proximally.

The distal catheter portion may have greater bending flexibility than the proximal catheter portion. In this way, it is ensured that the catheter tube is able to deflect easily into highly curved vessels. Thus points of treatment in highly tortuous vessels may also be reached easily.

In a particularly preferred embodiment of the invention, it is provided that the catheter tube has a smaller wall thickness in the distal catheter portion than in the proximal catheter portion. In other words, the wall thickness of the proximal catheter portion is larger than that of the distal catheter portion. In this way it is ensured that the proximal catheter portion has increased stiffness. Thus the catheter can be pushed easily into a blood vessel, since the advancing force in the proximal catheter portion is transmitted by the increased wall thickness along the longitudinal axis to the distal catheter portion. In this way, kinking of the proximal catheter portion is avoided. At the same time, the wall thickness in the proximal catheter portion enhances the insulating effect of the catheter tube, so that temperature-regulating fluid can be passed with small temperature loss as far as the distal catheter portion.

Preferably a linear relationship exists between the change of wall thickness and the change of cross-sectional diameter. The proximal catheter portion and the distal catheter portion therefore exhibit geometric similarity. In other words, the cross-sectional geometry of the distal catheter portion is formed by scaling of the cross-sectional geometry of the proximal catheter portion. Specifically, all cross-sectional dimensions (outside diameter, inner profile and wall thickness) are in a ratio to one another that is identical or at least similar in the proximal catheter portion and in the distal catheter portion.

In preferred embodiments of the invention, it is provided, moreover, that the catheter tube has a constant cross-sectional profile, especially a constant inside diameter. The difference between the outside diameter of the catheter tube in the distal catheter portion and in the proximal catheter portion is preferably obtained by a reduction of the wall thickness, especially without influencing the inside cross-sectional profile of the catheter tube. On the other hand, the inner cross-sectional profile may also extend unchanged over the entire length of the catheter tube. Preferably the inside diameter of the catheter tube is constant over the entire length.

The heat-exchanger element, especially the balloon, of the inventive medical catheter may be compressible in such a way that the heat-exchanger element in compressed condition has a cross-sectional diameter that corresponds at most to the outside diameter of the proximal catheter portion. Specifically, a receiving space for the heat-exchanger element may be formed on the distal catheter portion between an outer peripheral level of the distal catheter portion and an outer peripheral level of the proximal catheter portion. Thus this heat-exchanger element is compressible in such a way that the heat-exchanger element can be disposed completely inside the receiving space. A heat-exchanger element adapted in such a way ensures that the catheter tube has on the whole a maximum outside diameter determined by the outside diameter of the proximal catheter portion. The catheter tube has the largest outside diameter in the proximal catheter portion, so that the space inside a sheath can be used optimally in the distal catheter portion. The foregoing is true in particular in the case of use of the catheter with an additional sheath. In contrast, if no sheath is used for introduction of the catheter into a blood vessel, but instead the catheter itself forms a sheath, traumatization of tissue during introduction of the catheter into the blood vessel is reduced by the limitation of the outside diameter.

In particular, the heat-exchanger element may have a wall thickness of at most 30 µm, especially at most 25 µm, especially at most 20 µm, especially at most 15 µm. Preferably the wall thickness is 5 µm, especially at least 10 µm. The cross-sectional diameter of the heat-exchanger element is preferably at most 5 mm, especially at most 4.5 mm, especially at most 4.0 mm, especially at most 3.5 mm, especially at most 3 mm in the expanded condition. The lower limit for the cross-sectional diameter of the heat-exchanger element is preferably 2.5 mm. The cross-sectional diameter of the heat-exchanger element is preferably selected for application of the catheter such that in expanded condition it amounts to at most 50% of the inside cross-sectional diameter of the target vessel. In particular, the cross-sectional area of the expanded heat-exchanger element should be at most half of the inside cross-sectional area of the blood vessel at the point of treatment. In this way a sufficient blood flow around the heat-exchanger element is maintained during the treatment.

It is possible in principle for the catheter to have several heat-exchanger elements. In particular, it is possible for two, three, four, five or six heat-exchanger elements, for example balloons, to be disposed on the distal catheter portion. The length of the cylindrical middle part of the heat-exchanger elements or balloons in expanded condition is preferably between 10 mm and 40 mm, especially between 15 mm and 30 mm, preferably 20 mm. In the expanded condition, the cylindrical middle part is bounded by two conically shaped end portions on the longitudinal axis.

The taper angle (at the cone tip) is then between 20 degrees and 60 degrees, preferably 45 degrees. It is particularly advantageous when the length of the total distal catheter portion, i.e. from the first to the last heat-exchanger element or balloon, is between 40 mm and 120 mm, especially between 60 mm and 100 mm, preferably 80 mm. This length ensures that the space available in the common carotid artery (arteria carotis communis) can be used as well as possible.

In general it is possible to provide several heat-exchanger elements having different cross-sectional diameters. Preferably the cross-sectional diameter of the heat-exchanger elements is reduced in the direction of the longitudinal axis of the catheter. Then heat-exchanger elements disposed distally may respectively have a smaller cross-sectional diameter than proximally adjacent heat-exchanger elements. It is particularly preferred when at least one heat-exchanger element disposed most distally has a cross-sectional diameter that is so small that the heat-exchanger element while in expanded condition can be introduced into the internal carotid artery (arteria carotis interna). Within the distal catheter portion, it is also possible for one, two or three heat-exchanger elements disposed in a distal region of the distal catheter portion to have a smaller cross-sectional diameter in the expanded condition than do one or more heat-exchanger elements disposed in a proximal region of the distal catheter portion. In particular, the heat-exchanger elements with relatively small cross-sectional diameter, preferably disposed in the distal region of the distal catheter portion, may be introduced into the internal carotid artery, while on the other hand heat-exchanger elements with relatively large cross-sectional diameter, preferably disposed in the proximal region of the distal catheter portion, may remain in the common carotid artery.

The distal region of the distal catheter portion may have a length of between 20 mm and 60 mm, preferably 40 mm. The length of the proximal region of the distal catheter portion may be between 60 mm and 100 mm, especially 80 mm. The heat-exchanger elements in the distal region of the distal catheter portion preferably have, in the expanded condition, a cross-sectional diameter that is between 0.5 mm and 1.5 mm, especially 1 mm, smaller than in the proximal region of the distal catheter portion.

In other words, the cross-sectional diameter may be increased in the proximal direction from heat-exchanger element to heat-exchanger element, wherein the difference between the cross-sectional diameter of adjacent heat-exchanger elements is preferably between 0.5 mm and 1.5 mm. The difference in cross-sectional diameter between the most proximally disposed and the most distally disposed heat-exchanger elements is preferably between 0.5 mm and 3 mm, especially between 0.5 mm and 2 mm, especially between 0.5 mm and 1 mm.

If several heat-exchanger elements are provided in the distal catheter portion, they may have a distance from one another equal to at most 8 mm, especially at most 6 mm, especially at most 4 mm, especially at most 3 mm. Preferably the distance between two heat-exchanger elements is at least 1 mm, especially at least 2 mm. Within the meaning of the present disclosure, the distance between the heat-exchanger elements or balloons is determined between the points of contact of the heat-exchanger elements with the catheter tube or with the outer wall of the catheter tube.

Because of the limited distance between the heat-exchanger elements, it is ensured that, on the one hand, the space available in a blood vessel is used to good purpose and, on the other hand, high bending flexibility of the distal catheter portion is maintained. The heat-exchanger elements or balloons may be adhesively bonded to the catheter tube or heat-sealed onto it. It is also possible to produce the several balloons separately from one another or to form them in one piece. In the one-piece construction, it is provided that the balloons have tapered or narrowed regions, which are joined to the catheter. The supply of cooling fluid into the various balloons may take place in parallel or series manner. In series arrangement, the corresponding temperature-regulating lumen is sealed at the height of each individual balloon, so that the cooling fluid that emerges from a balloon and reenters the lumen is then diverted into the next balloon and does not form any shunt (bypass) due to the temperature-regulating lumen. As an example, the seal may be formed by an adhesive.

In general, the catheter may be provided with radiographic markers, which facilitate positioning of the catheter under radiographic control. The radiographic markers may be made in the form of coils or sleeves visible to x-rays. The sleeves may comprise a plastic, for example PU or Pebax, which is mixed with barium. As an example, the radiographic markers may be disposed upstream from the first (proximal) balloon and downstream from the last (distal) balloon, i.e. in the region of the catheter tip. However, it is also possible for the radiographic markers to be disposed between individual heat-exchanger elements or balloons. In particular, a radiographic marker between a proximal region and a distal region of the distal catheter portion may be positioned between two balloons. In this way the radiographic marker is able to distinguish optically between the balloons with relatively small cross-sectional diameter from the balloons with relatively large cross-sectional diameter. The radiographic markers may surround the catheter or be disposed inside a lumen. A combination (proximally around the catheter, distally inside a lumen) is also possible. The coil is preferably made of a platinum wire or a tantalum wire with a diameter between 40 and 250 µm, especially between 50 µm and 150 µm, preferably 100 µm.

Within the scope of the present invention, the catheter tube, in a first variant, may be formed in one piece. In particular, the catheter tube may be made in one piece by an extrusion process. By changing the extrusion parameters, the outside diameter of the catheter tube and thus the inside diameter of the through-lumen and of the temperature-regulating lumens as well as the wall thicknesses of the outer wall and of the inner separating walls are varied along the catheter tube. Moreover, the material for making the catheter tube may be changed in a single extrusion process, so that the distal catheter portion, for example, is softer or more flexible than the proximal catheter portion. In particular, the distal catheter portion may have a lower modulus of elasticity than the proximal catheter portion.

In a second variant, the catheter tube may have multi-piece, especially multi-layer structure. As an example, the catheter tube formed in one-piece may be produced by an extrusion process. In order to reduce the outside diameter in the distal catheter portion, the wall thickness of the catheter tube produced in one piece may be reduced in the distal catheter portion by a mechanical or laser-controlled ablation process. Alternatively, it may be provided that the reduced wall thickness or the reduced outside diameter in the distal catheter portion is already produced during the extrusion process.

In the multi-layer variant of the catheter tube, it may be specifically provided that the catheter tube has a multi-layer, especially two-layer outer wall at least in the proximal catheter portion. In the proximal catheter portion, the outer wall may be formed by an inner layer and an outer layer. The outer wall in the distal catheter portion may be formed by the inner layer. In particular, the outer wall in the distal catheter portion may be formed only by the inner layer. The inner and the outer layers are preferably joined to one another over their entire surface. For example, the outer layer may consist of a shrink-fitted tubing, a coating or a further tube. The outer catheter layer may be joined to the inner layer by a joining process, for example by lamination. In principle, the joint between the outer layer and the inner layer may be material-bonded or friction-bonded.

The outer and the inner layer may be of like or different materials. For example, it is possible for the outer layer and the inner layer to be produced together by a co-extrusion process, wherein the outer layer and the inner layer are made of different materials.

Because of the different layers, especially with different materials, the properties of the proximal catheter portion may be easily varied. For example, the outer layer may comprise a relatively hard material, so that the proximal catheter portion is reinforced by the outer layer. Furthermore, a material of low thermal conductivity may be chosen for the outer layer, in order to improve the insulation of the proximal catheter portion.

In a preferred embodiment, it is provided that the inner and/or the outer layer comprises a porous, especially spongy structure and/or hollow spheres. In particular, the outer layer may have a porous or spongy structure. Because of the porosity of the inner and/or outer layer, the thermal conductivity of the respective layer is reduced. In this way, temperature-regulating lumens can by thermally insulated effectively relative to the surroundings, especially blood floating around them. In this way uncontrolled heat transfer from the temperature-regulating fluid to the surroundings is prevented, especially in the proximal catheter portion.

At least the outer layer may have a thermal conductivity of lower than 0.2 $Wm^{-1}K^{-1}$, especially lower than 0.15 $Wm^{-1}K^{-1}$, especially lower than 0.1 $Wm^{-1}K^{-1}$, especially lower than 0.08 $Wm^{-1}K^{-1}$. In this way, improved thermal insulation is achieved in the proximal catheter portion, and so the thermal energy of the temperature-regulating fluid is released mainly in the region of the distal catheter portion.

In a further preferred embodiment, the catheter tube may have an outer tube and an inner tube. The outer tube may be larger than the inner tube, and so an insulating space is formed between the outer tube and the inner tube. In general, an insulating space may be kept clear between the outer tube or the outer layer and the inner tube or the inner layer. The insulating space may be formed by a gap or distance between the outer layer and the inner layer. In this way the insulating effect of the catheter tube is improved in the proximal catheter portion.

Preferably the outer tube and the inner tube are aligned eccentrically relative to one another. The gap or the insulating space then expediently extends at least in the region of the temperature-regulating lumens, in order to develop an insulating effect at least in this region of the catheter tube. The gap may have the greatest width in the region of the temperature-regulating lumens.

The outer tube and the inner tube may be joined to one another in places. Specifically, a joint line may be provided, which extends longitudinally axially along the catheter tube and along which the inner tube and the outer tube are joined to one another, especially by adhesive bonding or heat-sealing. Preferably the inner tube and the outer tube are joined to one another in the region of the through-lumen, wherein the through-lumen extends eccentrically through the catheter tube.

At least one spacer may be disposed between the outer tube and the inner tube, at least in the region of the temperature-regulating lumens. In this way an air volume, which leads to improved thermal insulation, is created between the outer tube and the inner tube.

The spacer may be formed by a shaped axial end of the outer tube. In particular, the outer tube may be shaped, for example crimped, at a distal end and be joined fluid-tightly to the inner tube. At the same time, the shaped end may function as a spacer. In principle, several spacers may be provided. In particular, both axial ends of the outer tube may constitute a spacer in the form of a crimped connection. Alternatively or additionally, spacers may be disposed between the axial ends of the outer tube. The spacers may be formed in one piece with the outer tube and/or the inner tube. It is also possible for at least one spacer that constitutes a separate component to be provided. For example, a ring that ensures a distance between the outer tube and the inner tube may be disposed between the outer tube and the inner tube.

In a further preferred embodiment of the present invention, at least the temperature-regulating lumens in the proximal catheter portion may have a larger cross-sectional area than in the distal catheter portion. In particular, the catheter tube may have on the whole an inside diameter that is larger in the proximal catheter portion than in the distal catheter portion. Preferably the wall thickness of the catheter tube is constant in this variant. Nevertheless, it is also possible for not only the cross-sectional area of the temperature-regulating lumens and/or of the through-lumen but also the wall thickness to vary along the catheter tube. In regard to simple and inexpensive production, it is particularly preferred when the dimensions of the distal catheter portion vary on the whole in direct proportion to the dimensions of the proximal catheter portion. In this way the distal catheter portion may constitute a scaled version of the proximal catheter portion.

Because the temperature-regulating lumens in the proximal catheter portion have a larger cross-sectional area than in the distal catheter portion, it is possible to pump a relatively high volume flow of temperature-regulating fluid through the catheter tube, since the relatively large cross-sectional area in the proximal catheter portion ensures that small pressure losses occur. Consequently the heat-exchanger function of the inventive catheter is improved.

Moreover, the catheter tube may be provided at a distal axial end with a catheter tip having a cross-sectional diameter that corresponds to or is larger than the cross-sectional diameter of the distal catheter portion. The catheter tip may at the same time form a seal for the temperature-regulating lumens. Specifically, the catheter tip is able to seal the temperature-regulating lumens fluid-tightly. Moreover, the catheter tip may have a through hole, which is aligned with the through-lumen. A heat-exchanger element, especially in the form of a compliant balloon, may be disposed between the catheter tip and the proximal catheter portion, i.e. in the distal catheter portion. The use of a catheter tip of the type described in the foregoing has the advantage that, while the catheter tube is being introduced into a blood vessel, the heat exchanger element, especially the balloon, has hardly any contact with the catheter sheath or the vessel wall. Thus a friction-inhibiting coating of the balloon, as is common in known balloon catheters, is not necessary. Heat transfer at the heat-exchanger element is improved by the absence of an additional, friction-inhibiting coating, since no additional heat transfer resistance due to the friction-inhibiting coating is present.

The catheter tip may be shaped, for example rounded. The two temperature-regulating lumens may be sealed by adhesive bonding or fusion.

In order to use the space inside the catheter tube to good purpose, it has proved advantageous to configure the temperature-regulating lumens in such a way that they have a cross-sectional profile resembling a pulmonary lobe. Specifically, each temperature-regulating lumen may have a cross-sectional profile resembling a pulmonary lobe. The cross-sectional profiles of the temperature-regulating lumens may be mirror images of one another. In this situation the through-lumen is preferably disposed eccentrically or laterally in the catheter tube.

The individual lumens of the catheter tube, especially the through-lumen and the temperature-regulating lumens, may be separated from one another by at least one inner wall. Preferably the inner wall is of stable or stiff structure, so that the cross-sectional areas of the temperature lumens remain substantially constant and in particular do not change due to the influence of forces or pressure. The inner wall is preferably flexible, so that the cross-sectional areas of the individual lumens are variable. In particular, the temperature-regulating lumens may be widened during the flow of a temperature-regulating fluid through them, especially by the fluid pressure. At the same time, the cross-sectional area of the through-lumen may shrink. In this way, the catheter tube may be further miniaturized.

In this connection it is pointed out that the catheter may in principle have several lumens. Thus further lumens, for example for filling of an occlusion balloon, for passage of sensor cables (temperature, pressure, partial pressure, $CO_2$ or $O_2$, flow, . . . ), or for administration of medications for lysis or neuroprotection as well as for administration of contrast agents or spasmolytics, may in addition to the temperature-regulating lumens or the through-lumen. Alternatively, administration may take place via the through-lumen.

A receiving region having a larger cross-sectional diameter than the through-lumen may be provided for a medical instrument in the distal catheter portion. Thus, for example, an expanded recanalization element, which has been guided through the through-lumen to a point of treatment, may be retracted into the catheter tube.

In the variant of the invention in which the catheter is designed to be advanced into a blood vessel via a sheath (catheter variant), a receiving region for a concretion or a thrombus may be provided in the distal catheter portion. The receiving region permits removal of the concretion or thrombus after recanalization.

In the alternative variant of the invention, in which the catheter itself acts as a sheath and in this respect is introduced directly into the blood vessel (sheath variant), the distal catheter portion may be designed without receiving region. The sheath variant is manipulated as follows: First a blood vessel is punctured, usually with a needle, to create an access to the blood vessel. Then a guide wire is introduced into the blood vessel and the needle is removed again. Now the catheter tube of the catheter is guided over the guide wire. After the guide wire has now been removed, a guide catheter, preferably of 5 French or 6 French size, is fed through the through-lumen. The actual recanalization element, for example a catch basket or stent-like system, is guided by a microcatheter, for example in 2 French, 2.5 French or 3 French size, inside the guide catheter to the point of treatment. Furthermore, a guide wire may be used for stabilization of the microcatheter and for location of the point of treatment. After the recanalization procedure, the thrombus may be aspirated into the guide catheter and refracted together with the guide catheter through the through-lumen. Alternatively or additionally, the aspiration or the removal of the thrombus may also take place through the through-lumen of the catheter tube. In this way the thrombus may be completely removed while the cooling process is being continued. It is also possible to push the microcatheter directly through the through-lumen and to retract the thrombus directly into the through-lumen, using aspiration if necessary. Moreover, it is conceivable to aspirate the thrombus directly into the guide catheter or the through-lumen of the catheter tube without using a recanalization element and/or microcatheter.

In the catheter variant, a marking may be provided in the proximal catheter portion to alert the user when the heat-exchanger element has reached the tip of the sheath or has already exited the sheath partly or completely. In other words, the distance from the catheter tip to the marking in the proximal catheter portion may correspond at least to the length of the sheath to be used.

In a particularly preferred embodiment, the through-lumen retains a constant diameter. In particular, the through-lumen may have the same constant cross-sectional diameters in the proximal catheter portion and in the distal catheter portion. Because of the receiving region, a flexible inner core, also known as a dilator, may be used to advance the catheter tube without the formation of a traumatic gap. To the contrary, the cross-sectional area of the transport lumens is reduced in the direction of the catheter tip, and so only the through-lumen remains at the catheter tip, i.e. the temperature-regulating lumens end upstream from the catheter tip. Consequently the catheter has particularly atraumatic behavior.

According to a second aspect, the invention is based on the idea of specifying a treatment system with a catheter as explained in the foregoing and a self-expandable device, especially a recanalization element, which is joined to an elongated guide element and is disposed to be longitudinally displaceable together with the guide element in the through-lumen. In this combination, the catheter may be used, for example, for cooling of blood, while at the same time a thrombus is being removed from the blood. The guide element may be formed by a transport wire.

In the catheter variant, the recanalization element is preferably guidable via a microcatheter to the point of treatment, in which case the microcatheter can be pushed to the point of treatment through a guide catheter disposed in the through-lumen of the catheter tube. By means of the transport wire, which may be guided through the microcatheter, the recanalization element may be moved to the point of treatment. The recanalization element may form a receiving region for a thrombus. In the sheath variant, an aspiration catheter, for example in 5 French or 6 French size, may be guided through the through-lumen of the catheter tube and thus a thrombus may be removed via the through-lumen.

Further in the scope of the present application, a treatment system is disclosed and claimed that has a catheter as described in the foregoing and a guide catheter, which is disposed or can be positioned by longitudinal displacement inside the through-lumen of the catheter tube. In this situation, moreover, the catheter may preferably take over the function of a sheath, which is then made unnecessary. A further aspect of the invention relates to a method for producing the catheter and/or treatment system described in the foregoing, wherein an inner tube is disposed inside an outer tube in such a way that an end portion of the inner tube protrudes distally from the outer tube, and wherein at least a distal end of the outer tube is joined fluid-tightly to the inner tube, especially by shrink-fitting, adhesive bonding or heat-sealing. The inventive method simplifies the production and permits rapid and simple adaptation of the catheter. For example, outer tubes of different length can be combined with inner tubes of different length. Thus the length of the distal catheter portion can be changed rapidly during the production process.

It is possible in principle, and within the scope of the invention it is also claimed, that a method for producing the catheter and/or treatment system described in the foregoing comprises an extrusion process, wherein the catheter tube is extruded in one piece from a single material or different materials.

BRIEF DESCRIPTION OF THE DRAWINGS

The invention will be explained in more detail hereinafter on the basis of exemplary embodiments with reference to the attached schematic drawings, wherein

FIG. 4 Shows a schematic side view of the catheter tube according to FIG. 1;

FIG. 5 shows a cross section through a proximal catheter portion of a one-piece catheter tube;

FIG. 6 shows a cross section through the proximal catheter portion of a multi-layer catheter tube;

FIG. 7 shows a cross section through the proximal catheter portion of a multi-layer catheter tube, wherein spacers are provided to form an insulating space;

FIG. 8 shows a cross section through a proximal catheter portion of a catheter tube, wherein an annular, continuous insulating space is provided between an outer tube and an inner tube;

FIG. 9 shows a longitudinal-sectional view through the catheter tube according to FIG. 8;

FIG. 16a shows a side view of a catheter tube of the inventive catheter according to a preferred exemplary embodiment;

FIG. 16b and FIG. 16c respectively show a cross-sectional view through the catheter tube according to FIG. 16;

FIG. 17a shows a longitudinal-sectional view through a catheter tube of an inventive catheter according to a further preferred exemplary embodiment with a dilator disposed in the through-lumen;

FIG. 17b shows a cross-sectional view of the catheter tube according to FIG. 17a, with the section line marked;

FIG. 17c and FIG. 17d respectively show a cross-sectional view through the catheter tube according to FIG. 17a;

FIG. 17e shows a cross-sectional view through the dilator according to FIG. 17a;

FIG. 18a shows a longitudinal-sectional view through a catheter tube of the catheter according to FIG. 17a;

FIG. 19a shows a further longitudinal-sectional view through the catheter tube according to FIG. 18a;

DETAILED DESCRIPTION OF THE INVENTION

Figure 1:
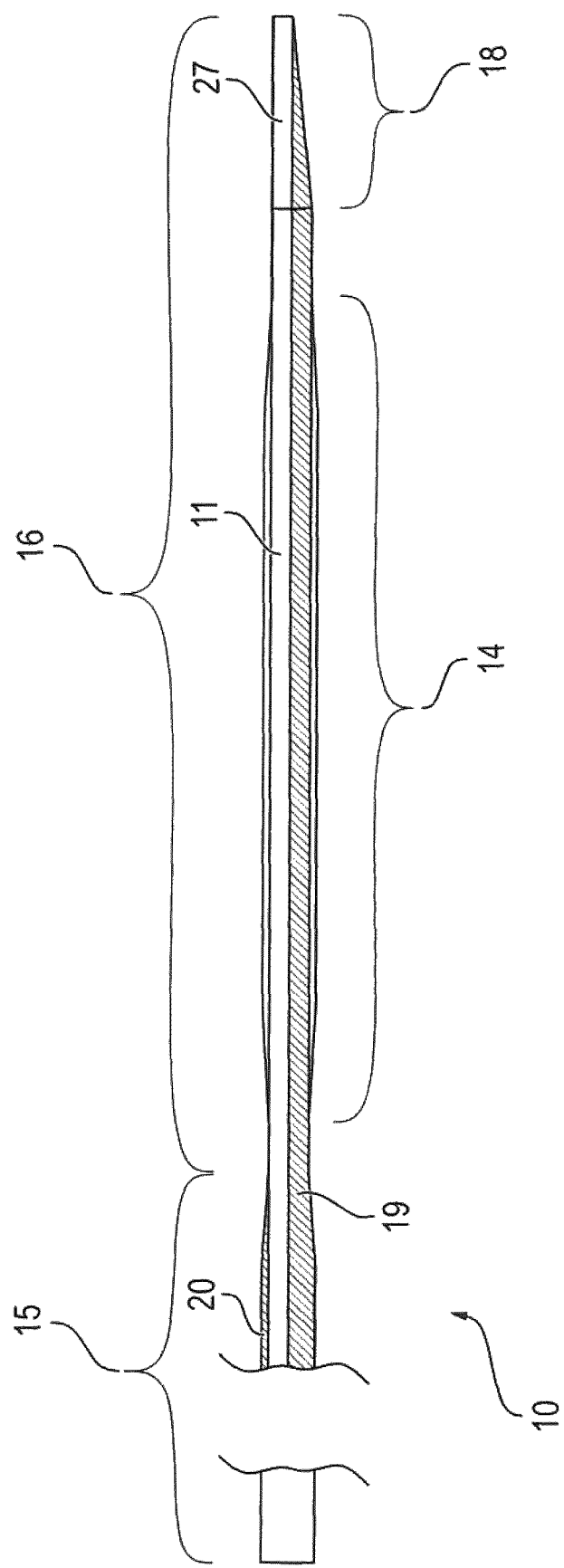
FIG. 1 shows a longitudinal section through the catheter tube of an inventive catheter according to a preferred exemplary embodiment.

FIG. 1 shows a catheter tube 10 of an inventive catheter, wherein catheter tube 10 has a proximal catheter portion 15 and a distal catheter portion 16. Distal catheter portion 16 comprises a catheter tip 18. In distal catheter portion 16, a heat-exchanger element 14 is disposed proximal to catheter tip 18. Heat-exchanger element 14 is preferably designed as an expandable balloon.

Figure 2:
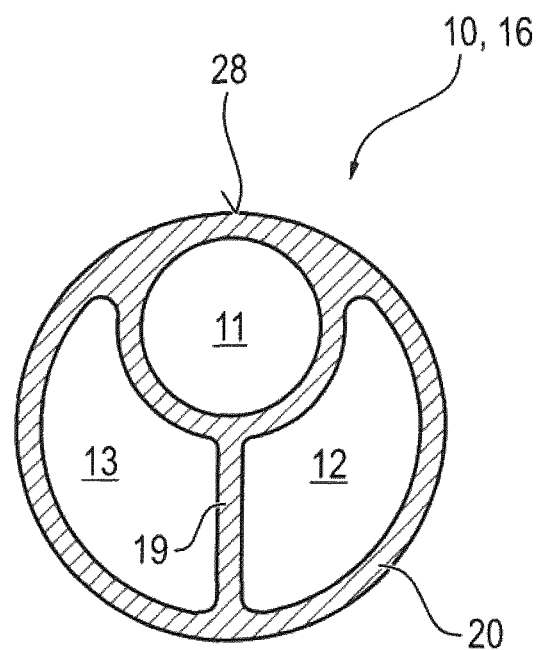
FIG. 2 shows a cross section through the catheter tube according to FIG. 1 in the proximal catheter portion.

FIG. 2 shows a cross section through catheter tube 10 according to FIG. 1 in the transition region between catheter tip 18 and the part of distal catheter portion 16 supporting heat-exchanger element 14. In principle, the catheter tube has, in distal catheter portion 16, especially also in the region of heat-exchanger element 14, a cross section according to FIG. 2.

Catheter tube 10 has on the whole an outer wall 20, which bounds catheter tube 10 on the outside. At the same time, outer wall 20 forms a boundary for three lumens 11, 12, 13, which extend longitudinally axially through catheter tube 10. In particular, catheter tube 10 has a through-lumen 11, which extends completely through catheter tube 10. Through-lumen 11 has circular cross section. Preferably through-lumen 11 is used as an instrument lumen, i.e. for advancing instruments through catheter tube 10 to a point of treatment. Such instruments may comprise, for example, a recanalization device or in general a self-expandable element. Through-lumen 11 is disposed eccentrically relative to the longitudinal axis of catheter tube 10.

Furthermore, catheter tube 10 is provided with two temperature-regulating lumens 12, 13. The temperature-regulating lumens not only are bounded by outer wall 20 but also are separated from one another and from through-lumen 11 by an inner wall 19. Inner wall 19 extends through the catheter tube and preferably has a Y-shaped cross section. Temperature-regulating lumens 12, 13 respectively have cross sections resembling pulmonary lobes.

The longitudinal section according to FIG. 1 cuts through through-lumen 11 and inner wall 19, and so the temperature-regulating lumens are not visible in FIG. 1. In contrast, the balloon forming heat-exchanger element 14 is clearly visible in FIG. 1. Heat exchanger element 14 is compressed or collapsed and thus increases the outside dimensions of catheter tube 10 in regions of distal catheter portion 16. Moreover, it can be clearly seen in FIG. 1 that catheter tube 10 has a smaller cross-sectional diameter in distal catheter portion 16 than in proximal catheter portion 15. In this way, within distal catheter portion 16, sufficient space outside the catheter tube is created in radial direction relative to catheter tube 10 in order to receive the compressed balloon or compressed heat-exchanger element 14. Specifically, heat-exchanger element in the compressed or collapsed condition has on the whole outside dimensions that are not larger than the cross-sectional diameter or the outside dimensions of catheter tube 10 in proximal catheter portion 15. Thus heat-exchanger element 14, when in compressed or collapsed condition, may have an outside dimension that is smaller than or at most just as large as the outside dimension of proximal catheter portion 15.

In general, it may be provided that inner wall 19 is flexible. In particular, several flexible inner walls 19 separating individual lumens 11, 12, 13 from one another may be disposed inside catheter tube 10. Because of the flexibility of the inner walls, temperature-regulating lumens 12, 13 are able to dilate, in order to permit a higher volume flow of a temperature-regulating fluid. To guide an instrument through through-lumen 11, it is possible to compress temperature-regulating lumens 12, 13, for example by creating a partial vacuum, so that through-lumen 11 is correspondingly widened. It is preferable when the inner walls of catheter tube 10 are sufficiently stable that deformation of through-lumen 11 and/or of temperature-regulating lumens 12, 13 is prevented. Nevertheless, catheter tube 10 preferably has high bending flexibility.

Alternatively or additionally, a receiving region adapted to receive a medical instrument, especially an expanded instrument, may be provided in distal catheter portion 16. The receiving region preferably has a cross-sectional area larger than the cross-sectional area of through-lumen 11. In particular, inner wall 19 may end at a distance from the distal end of catheter tube 10, so that catheter tube 10 is substantially free of internals in the receiving region.

Furthermore, it can be seen in FIG. 1 that the wall thickness of outer wall 20 is larger in proximal catheter portion 15 than in distal catheter portion 16. At the same time, outer wall 20 functions as an insulating member, so that temperature losses in proximal catheter portion 15 are prevented while a temperature-regulating fluid is flowing through it.

As regards catheter tip 18, it is provided that is has a conical geometry. The conical geometry of catheter tip 18 may be asymmetric, so that a through hole 27, which extends through catheter tip 18, is linearly aligned with through-lumen 11. In the exemplary embodiment according to FIG. 1, catheter tip 18 has an outside diameter that at most corresponds to the outside diameter of distal catheter portion 16.

Figure 3:
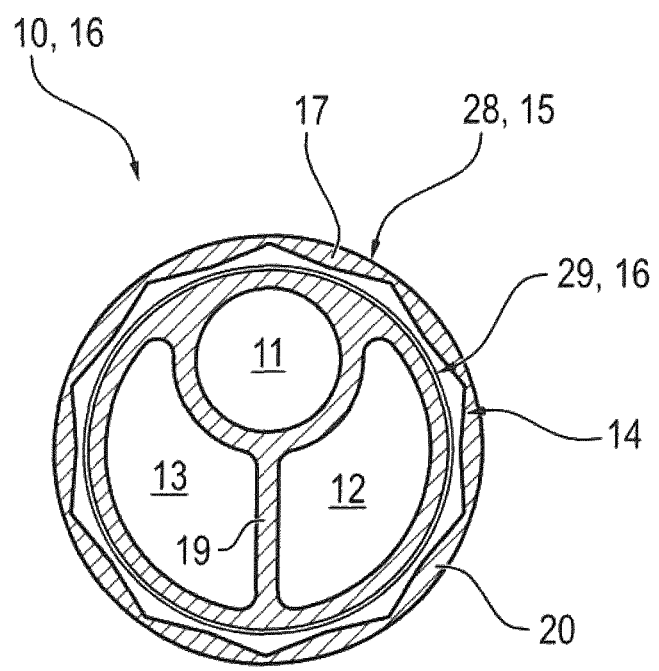
FIG. 3 shows a cross section through the catheter tube according to FIG. 2 in the distal catheter portion.

FIG. 3 shows a further cross section through catheter tube 10 according to FIG. 1. A cross section through distal catheter portion 16 containing heat-exchanger element 14 is illustrated. It is readily visible that outer wall 20 has a larger outside diameter in proximal catheter portion 15 than does outer wall 20 in distal catheter portion 16. Specifically, outer wall 20 in proximal catheter portion 15 forms a cylindrical proximal outer peripheral level 28. In distal catheter portion 16, outer wall 20 forms a distal outer peripheral level 29. An annular receiving space 17 is formed between proximal outer peripheral level 28 and distal outer peripheral level 29. Compressed or collapsed heat-exchanger element 14 is disposed inside receiving space 17, which is bounded radially inwardly by distal outer peripheral level 29 and radially outwardly by proximal outer-peripheral level 28. In other words, heat exchanger element 14 or the balloon may be sufficiently compressible or foldable that heat-exchanger element 14 can be disposed completely inside receiving space 17.

It is expedient when heat-exchanger element 14 in the compressed or collapsed condition does not protrude radially outward beyond proximal outer peripheral level 28. To the contrary, proximal outer peripheral level 28 of outer wall 20 in proximal catheter portion 15 forms the largest cross-sectional diameter of the entire catheter tube 10. The compressed or collapsed condition is preferably achieved or maintained by application of external forces. For example, a sheath in which catheter tube 10 is disposed may form a boundary, which prevents expansion of heat-exchanger element 14, especially of a balloon.

As regards heat-exchanger element 14, it is preferably provided that this is formed by an expandable balloon. On the one hand the balloon may be collapsed to compressed condition, but when filled with a temperature-regulating fluid may be dilated to its nominal size. Such a balloon is produced in the widened or expanded condition and is compressed by collapsing it. The balloon therefore exhibits "non-compliant" behavior. In this connection, the cross-sectional diameter of the balloon increases at a relative internal pressure of 2 bar by at most 10%, especially at most 5%, especially at most 2.5%, especially at most 1% compared with the fully expanded condition of the balloon (relative internal pressure approximately 0.1 bar to 0.2 bar). Alternatively, a so-called compliant balloon comprising an elastic material may be used. Such balloons are produced in the compressed condition. The elastic balloon is dilated radially by a fluid pressure and shrinks to the original nominal size upon relaxation of the fluid pressure.

In general, heat-exchanger element 14 or the balloon is in fluidic communication with temperature-regulating lumens 12, 13. For this purpose, outer wall 20 preferably has two fluid openings 33, 34, wherein each of the two fluid openings 33, 34 is respectively allocated to a temperature-regulating lumen 12, 13. Both fluid openings 33, 34 discharge into the balloon or heat-exchanger element 14. On the whole, a temperature-regulating circuit is established in this way. In this case a first temperature-regulating lumen 12 may form a fluid-supply line and a second temperature-regulating lumen 13 a fluid-return line. Temperature-regulating fluid, preferably a cooling medium, may flow via first temperature-regulating lumen 12 to heat-exchanger element 14 or balloon. The temperature-regulating fluid flows through the balloon, preferably from distally to proximally, and passes via a proximal fluid opening 34 in outer wall 20 into second temperature-regulating lumen 13. Via a second temperature-regulating lumen 13 or the fluid-return line, the temperature-regulating fluid is discharged from catheter tube 10.

The principle of the invention is schematically illustrated once again in FIG. 4. Catheter tube 10, illustrated in simplified form, generally has a proximal catheter portion 15 and a distal catheter portion 16. A collapsed balloon is disposed as heat-exchanger element 14 in distal catheter portion 16. The balloon or heat-exchanger element 14 is supported by distal catheter portion 16 of catheter tube 10. Specifically, heat-exchanger element 14 in collapsed condition is arranged in such a way that it is disposed inside a receiving space 17, which is bounded in radial direction on the one hand by proximal outer peripheral level 28 and on the other hand by distal outer peripheral level 29.

In principle, catheter tube 10 may be produced in one part or in one piece. This may take place on the one hand by an appropriate extrusion method. On the other hand, catheter tube 10 may be produced with a uniform, relatively larger wall thickness of outer wall 20. In a subsequent processing step, the wall thickness, starting from the outer periphery, may be reduced sufficiently by a mechanical or laser-assisted ablation process in distal catheter portion 16 that distal catheter portion 16 ultimately has smaller outside dimensions than proximal catheter portion 15.

Figure 12:
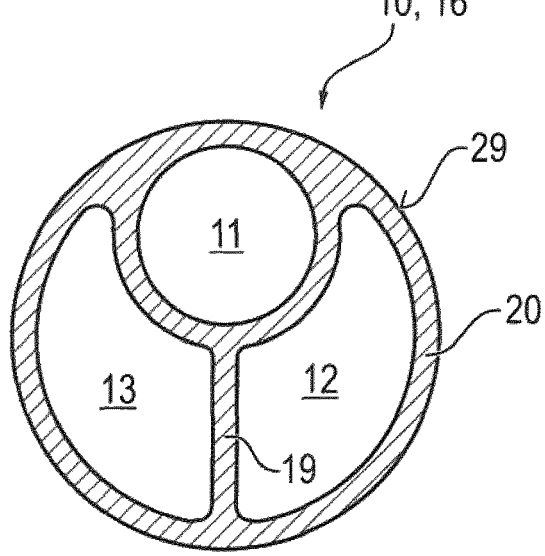
FIG. 12 shows a cross-sectional view through the distal catheter portion of a catheter tube according to FIGS. 5 to 11.

For the example of a catheter tube 10, which is formed in one part, FIG. 5 shows a cross section through proximal catheter portion 15, wherein it can be seen that proximal catheter portion 15 has relatively large wall thickness. In contrast, FIG. 12 shows a cross section through the same catheter tube 10 in distal catheter portion 16. It is clearly visible that outer wall 20 of catheter tube 10 in distal catheter portion 16 has a smaller wall thickness than in proximal catheter portion 15. The dimensions of lumens 11, 12, 13 are preferably identical. In other words, catheter tube 10 on the whole has a constant inside diameter. Only the outside diameter of catheter tube 11 varies and is accompanied by a corresponding variation of the wall thickness of outer wall 20.

Because of the reduced wall thickness of outer wall 20 in distal catheter portion 16, distal catheter portion 16 is more flexible in bending than proximal catheter portion 15. This makes it possible to advance catheter tube 10 into small and narrowly tortuous blood vessels. Improved advancability into small and narrowly tortuous blood vessels, especially good bending flexibility of catheter tube 10, is also obtained in the preferred configuration, in which distal catheter portion 16 is a scaled version of proximal catheter portion 15, i.e. when the cross-sectional areas of temperature-regulating lumens 12, 13 in distal catheter portion 16 are also smaller than in proximal catheter portion 15.

The increased wall thickness of outer wall 20 in proximal catheter portion 15 stiffens proximal catheter portion 15, and so catheter tube 11 can on the whole be readily pushed along the longitudinal axis. Consequently, an advancing force applied at the proximal axial end is transferred effectively to catheter tip 18. At the same time, the increased wall thickness of outer wall 20 in proximal catheter portion 15 provides an improved insulating effect, and so temperature losses are prevented during flow through temperature-regulating lumens 12, 13 in proximal catheter portion 15. This increases the efficiency of the local temperature regulation or cooling at heat-exchanger element 14. In the catheter variant in which catheter tube 10 is produced in one piece, for example via an extrusion process, materials such as polyurethane, Pebax, nylon, thermoplastic plastics, especially thermoplastic elastomers are preferably used. In this respect, PTFE or other fluoro polymers are advantageous, since in this way the friction against a sheath and/or the vessel wall is reduced. However, it is difficult to line these materials with heat-exchanger element 14 or balloon. In that respect, nylon or PET are expedient as the material for the balloon.

Instead of a one-part structure of catheter tube 10, this may also be of multi-part structure. In particular, catheter tube 10 may comprise an inner tube 23, which extends completely through proximal catheter portion 15 and distal catheter portion 16. Inner tube 23 may have constant cross section, especially in the form of the cross section according to FIG. 12. In order to increase the outside diameter in proximal catheter portion 15 and thus to create a diameter difference between proximal catheter portion 15 and distal catheter portion 16, inner tube 23 may be provided with an additional layer in proximal catheter portion 15. Specifically, it may be provided that catheter tube 10 or outer wall 20 is of multi-layer structure in proximal catheter portion 15, in which case at least one inner layer 21 and one outer layer 23 are provided.

Inner layer 21 is preferably formed by inner tube 23. Outer layer 22 may be formed by a shrink-fitted tube, a full-surface covering, especially a coating, or by a further tube, which is joined to inner tube 23 by lamination, for example. In any case, full-surface, preferably material-bonded contact exists between inner layer 21 and outer layer 22. Outer layer 22 and inner layer 21 may be formed from different materials.

Inner layer 21 and outer layer 22 may be produced simultaneously by a coextrusion process. Alternatively, inner tube 23 or inner layer 21 may be produced first and then outer layer 22 applied onto inner layer 21 in proximal catheter portion 15. Outer layer 22 may contain fillers, reinforcing substances or other additives, in order to impart properties other than those of inner layer 21 to outer layer 22. In particular, outer layer 22 may form a reinforcing layer, in order to increase the longitudinal axial stability of outer wall 20 in proximal catheter portion 15. For example, outer layer 22 may contain nano-reinforced composite materials, which comprise, for example, nylon, thermoplastic elastomers or thermoplastic polyurethanes. Furthermore, reinforcement of proximal catheter portion 15 may be achieved by using for outer layer 22 a material that is harder than the material of inner layer 21. Outer layer 22 may also comprise a wire mesh (braid) or a spirally wound wire (coil) as reinforcing element.

For improved thermal insulation, it is preferable for outer layer 22 to be of a material with low thermal conductivity. In particular, it may be provided that the outer layer has a thermal conductivity of at most 0.2 $Wm^{-1}K^{-1}$, especially at most 0.15 $Wm^{-1}K^{-1}$, especially at most 0.1 $Wm^{-1}K^{-1}$, especially at most 0.08 $Wm^{-1}K^{-1}$.

In general, outer layer 22 may be formed as an additional tube, especially as outer tube 24. Outer tube 24 may have an inside diameter larger than an outside diameter of inner tube 23. Preferably outer tube 24 is pushed over inner tube 23 in the region of proximal catheter portion 15 and joined to inner tube 23 at least at one distal axial end. For example, the distal axial end of outer tube 24 may be shrink-fitted or crimped in order to create a fluid-tight joint with inner tube 23. Outer tube 24 may also be joined to inner tube 23 by adhesive bonding or heat-sealing.

The crimped axial end may form a spacer 25, which holds open a gap or insulating space 26 between outer tube 24 and inner tube 23. Other types of spacers 25 are possible. In particular, several spacers 25 may be disposed along outer tube 24, in such a way that they are joined in one piece to outer tube 24 or inner tube 23 or are disposed separately, for example as rings, between outer tube 24 and inner tube 23. Independently of the type and geometry of spacers 25, it is provided that insulating space 26 amounts to a radial height, i.e. outer tube 24 and inner tube 23 are spaced apart from one another by at least 50 μm, especially at least 100 μm, especially at least 150 μm.

FIG. 7 shows an exemplary embodiment in which catheter tube 10 in proximal catheter portion 15 is provided with radially inwardly projecting spacers 25, so that an insulating space 26 is formed between outer tube 24 and inner tube 23. Preferably several spacers 25 extend over the periphery of inner tube 23. Spacers 25 may be formed on the one hand as radially inwardly projecting elements of outer tube 24 and on the other hand as radially outwardly projecting elements of inner tube 23. Insulating space 26 preferably forms an air space, which contributes to improved insulation of outer wall 20 in proximal catheter portion 15. In general, spacers 25 may be disposed between inner tube 23 and outer tube 24 at least in the region of temperature-regulating lumens 12, 13. In the exemplary embodiment according to FIG. 7, spacers 25 are disposed over the entire periphery of inner tube 23, so that outer tube 24 and inner tube 23 are spaced apart coaxially relative to one another, in order to form insulating space 26.

Insulating space 26 may also be formed without the use of spacers 25. FIG. 8 shows such an exemplary embodiment. Specifically, a cross section through a proximal catheter portion 15 of a catheter tube 10 is shown in FIG. 8, wherein outer wall 20 of catheter tube 10 in proximal catheter portion 15 is formed by an inner tube 23 and an outer tube 24. Outer tube 24 and inner tube 23 are disposed coaxially with one another and are radially spaced apart from one another. In this way an annular insulating space 26 is formed between outer tube 24 and inner tube 23.

A longitudinal section through catheter tube 10 according to FIG. 8 is shown in FIG. 9. Catheter tube 10 comprises a proximal catheter portion 15 and a distal catheter portion 16. Inner tube 23 extends over the entire length of catheter tube 10, especially through proximal catheter portion 15 and distal catheter portion 16. Outer tube 24 extends exclusively along proximal catheter portion 15. Outer tube 24 forms a proximal outer peripheral level 28, which radially outwardly bounds a receiving space 17 disposed in distal catheter portion 16. Receiving space 17 is bounded radially inwardly by a distal outer peripheral level 29, which is defined by inner tube 23. Outer tube 24 is disposed coaxially relative to inner tube 23, wherein a distance exists between outer tube 24 and inner tube 23. The distance between outer tube 24 and inner tube 23 is filled by an insulating space 26. In order to close off insulating space 26, a proximal closure flange 30 is provided at the proximal end of catheter tube 10. A distal closure flange 31 is provided at the distal end of proximal catheter portion 15. Closure flanges 30, 31 are of substantially annular structure and close off insulating space 26 fluid-tightly in distal and proximal direction. For this purpose, closure flanges 30, 31 join inner tube 23 to outer tube 24.

Figure 10:
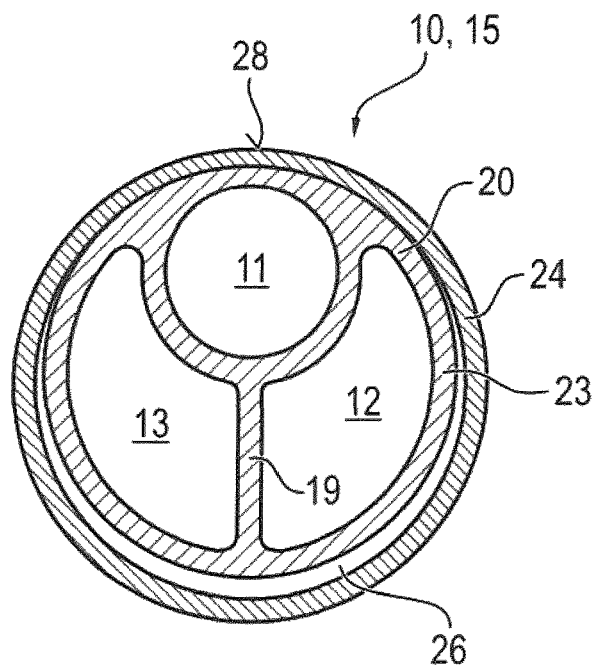
FIG. 10 shows a cross-sectional view through the proximal catheter portion of an inventive medical catheter according to a further preferred exemplary embodiment, wherein the catheter tube has an inner tube and an eccentrically disposed outer tube.

A further exemplary embodiment of the inventive medical catheter is shown in FIG. 10. In particular, a cross section through catheter tube 10 in proximal catheter portion 15 is illustrated. Within proximal catheter portion 15, catheter tube 10 has an inner tube 23 and an outer tube 24, wherein outer tube 24 is disposed eccentrically relative to inner tube 23. In particular, outer tube 24 bears on inner tube 23 in the region of through-lumen 11 or of the instrument lumen. Preferably outer tube 24 is firmly joined to inner tube 23 at this place, for example by heat-sealing or adhesive bonding. In contrast, in the region of temperature-regulating lumens 12, 13, outer tube 24 is spaced apart from inner tube 23. In this way an insulating space 26 between outer tube 24 and inner tube 23 is formed at least in the region of temperature-regulating lumens 12, 13.

Figure 11:
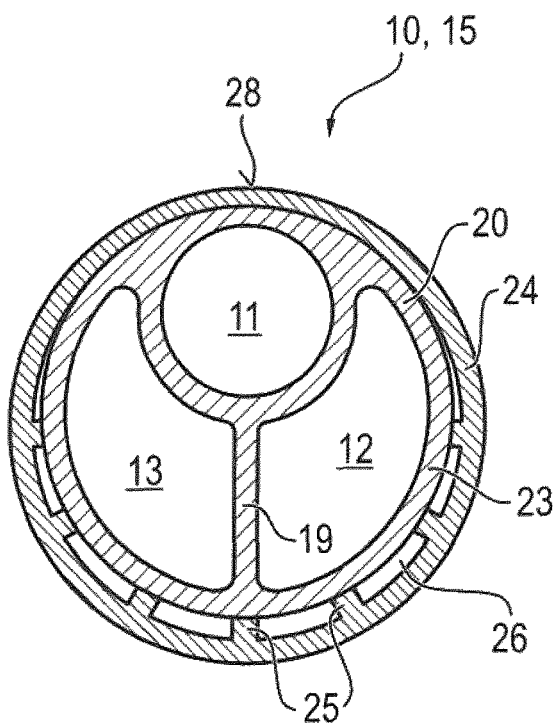
FIG. 11 shows a cross-sectional view through a further catheter tube with an inner tube and an outer tube, wherein spacers are disposed between the inner tube and the outer tube.

In order to ensure that a distance, especially an insulating space 26, exists between outer tube 24 and inner tube 23, spacers 25 may be disposed between outer tube 24 and inner tube 23, at least in the region of temperature-regulating lumens 12, 13. Such an exemplary embodiment, in which outer tube 24 is disposed eccentrically relative to inner tube 23 and in the region of temperature-regulating lumens 12, 13 is held at a distance from inner tube 23 by spacers 25, is shown in FIG. 11. By analogy with the exemplary embodiment according to FIG. 7, spacers 25 may be joined to or formed in one piece with outer tube 24 and also in one piece with inner tube 23. In any case, an insulating space 26 exists between inner tube 23 and outer tube 24 in the region of temperature-regulating lumens 12, 13. For this purpose it is not necessary to provide several spacers 25. To the contrary, a single spacer 25 may be sufficient to create a durable distance between outer tube 24 and inner tube 23. Preferably single spacer 25 is disposed (radially) opposite a joint between outer tube 24 and inner tube 23.

FIG. 12 shows a cross section through catheter tube 10 in distal catheter portion 16. Within distal catheter portion 16, catheter tube 10 also has a through-lumen 11 and two temperature-regulating lumens 12, 13, which are separated from one another by an inner wall 19. Catheter tube 10 further comprises an outer wall 20, which has a relatively thin wall thickness. In particular, outer wall 20 is of single-layer structure in distal catheter portion 16. Outer wall 20 forms a distal outer peripheral level 29 of catheter tube 10.

For all exemplary embodiments according to FIGS. 5 to 11, which respectively show proximal catheter portion 15, it is appropriate for the corresponding or associated distal catheter portion 16 to have a geometry according to FIG. 12. In other words, FIG. 12 shows a distal catheter portion 16 of catheter tube 10 according to one of FIGS. 5 to 11. For this purpose, distal catheter portion 16 according to FIG. 12 may be formed in one piece with proximal catheter portion 15 according to FIG. 5. Alternatively, one of the exemplary embodiments according to FIGS. 6 to 11 may be formed with an inner tube 12 that has a cross-sectional geometry according to FIG. 12 and extends beyond proximal catheter portion 15 in order to form distal catheter portion 16.

In general, it is possible to provide that, in the exemplary embodiments according to FIGS. 6 to 11, outer layer 22 or outer tube 24 may be configured in such a way that the thermal conductivity is reduced. For example, outer layer 22 or outer tube 24 may have a porosity, especially a foam-like structure. This may be achieved, for example, by incorporation of microbubbles during the extrusion process. Alternatively, hollow microspheres may be incorporated in the material of outer tube 24 or of outer layer 22. On the whole, it is preferable for outer tube 24 or outer layer 22 to have cavities in which air may be received. In this way the insulating effect of outer layer 22 or of outer tube 24 is improved. Alternatively, elastomers, insulating foam layers of cross-linkable copolymers may be used for the insulation. Preferably such materials are integrated into outer layer 22 or outer tube 24. The elastomeric, insulating foam layers may contain, for example, polyethylene and polypropylene units or polyethylene-propylene diene.

Figure 13:
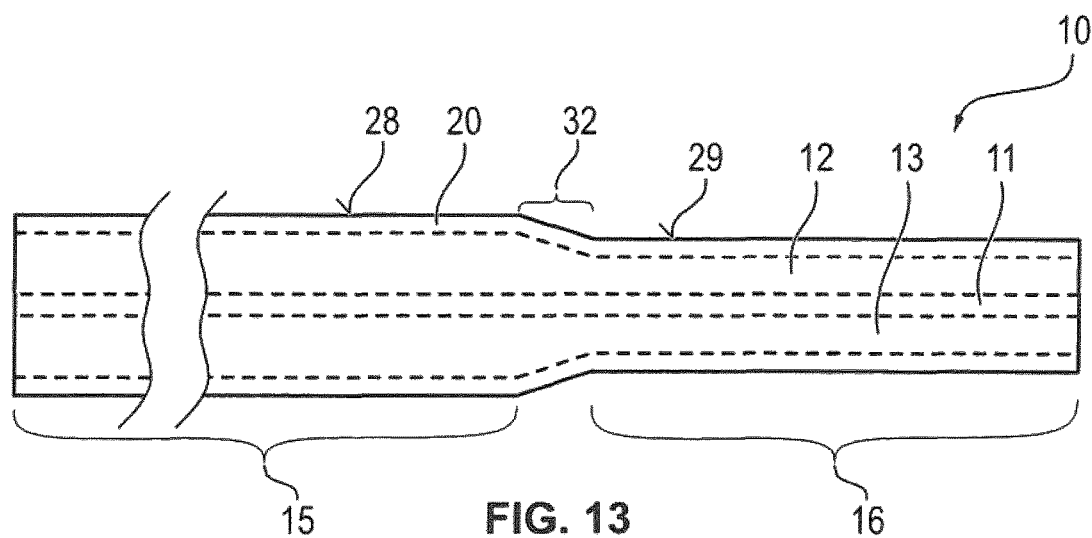
FIG. 13 shows a longitudinal-sectional view through a catheter tube of the inventive catheter according to a further preferred exemplary embodiment, wherein the temperature-regulating volume in the proximal catheter portion have a larger cross-sectional area than in the distal catheter portion.

An alternative exemplary embodiment of the inventive catheter is shown in FIG. 13. In contrast to the foregoing exemplary embodiments, the wall thickness in the exemplary embodiment according to FIG. 13 is not varied along catheter tube 10, but instead the inside cross-sectional diameter of catheter tube 10 is reduced in distal catheter portion 16 compared with proximal catheter portion 15. Specifically, temperature-regulating lumens 12, 13 in distal catheter portion 16 have a smaller cross-sectional area than in proximal catheter portion 15. In contrast, the wall thickness of outer wall 20 may be constant along entire catheter tube 10.

Likewise the cross-sectional area of through-lumen 11 is preferably constant along entire catheter tube 10. Nevertheless, it is also possible for both the wall thickness and the cross-sectional areas of the individual lumens 11, 12, 13 to vary along catheter tube 10. Temperature-regulating lumens 12, 13 may have a larger cross-sectional area in proximal catheter portion 15 than in distal catheter portion 16. Thus the volume of temperature-regulating fluid that can be passed through the temperature-regulating circuit may be increased. This optimizes the heat-exchanger function of the entire catheter. In order to improve the advancability of the catheter or catheter tube 10, it is provided that a conical transition portion 32 is formed between proximal catheter portion 15 and distal catheter portion 16. The length of conical transition portion 32 is preferably at most 120 mm, especially at most 100 mm, especially at most 80 mm, especially at most 60 mm, especially at most 40 mm, especially at most 30 mm, especially at most 20 mm. At a minimum, the length of conical transition portion 32 is preferably 10 mm.

Figure 14:
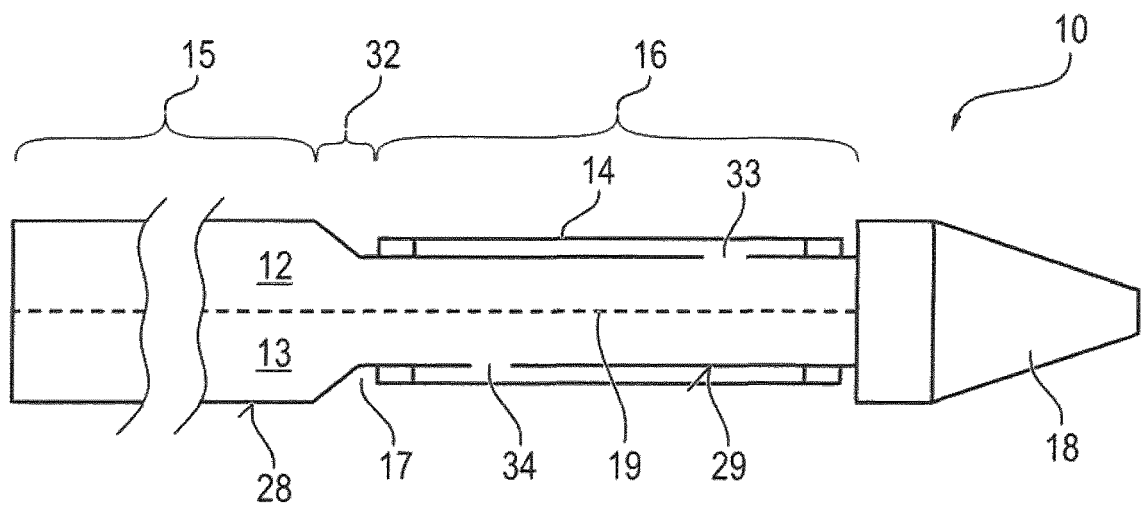
FIG. 14 shows a longitudinal-sectional view through an inventive catheter according to a further preferred exemplary embodiment with a catheter tip disposed at the distal axial end, wherein a balloon in the compressed condition is disposed as the heat-exchanger element between the catheter tip and the proximal catheter portion.
Figure 15:
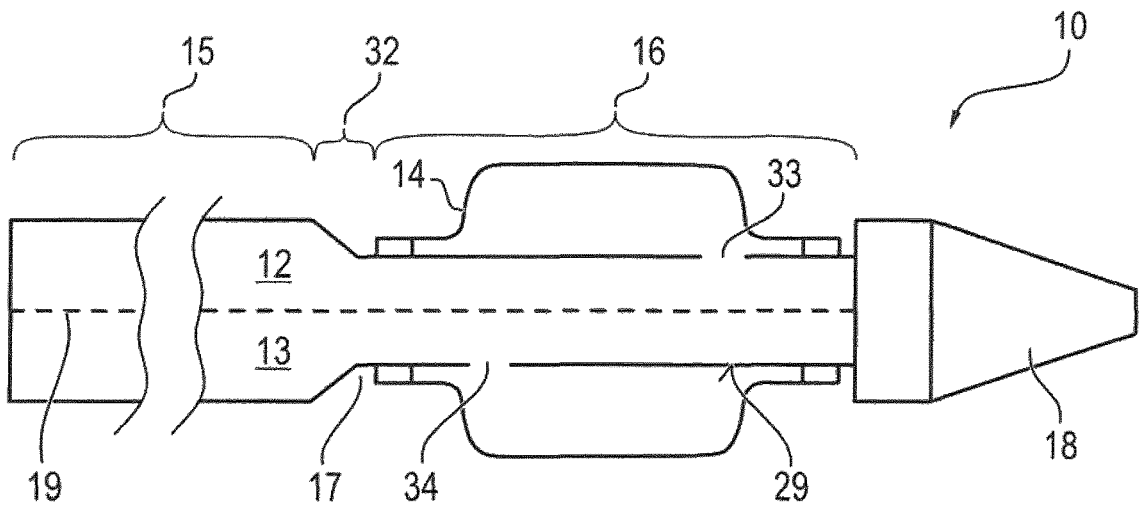
FIG. 15 shows the longitudinal-sectional view according to FIG. 14, wherein the balloon is displayed in expanded condition.
Figure 18B:
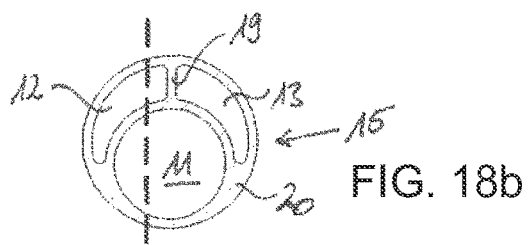
FIG. 18b shows a cross-sectional view through the catheter tube according to FIG. 18a, with the section line marked.
Figure 18A:
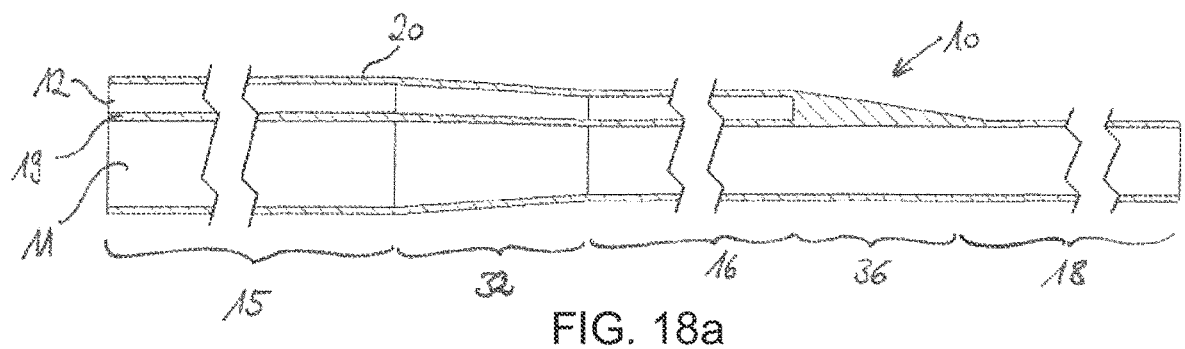
Figure 19B:
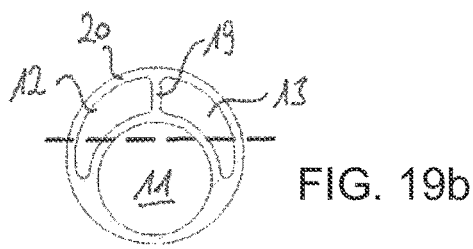
FIG. 19b shows a further cross-sectional view through the catheter tube according to FIG. 19a, with the section line marked.
Figure 19A:
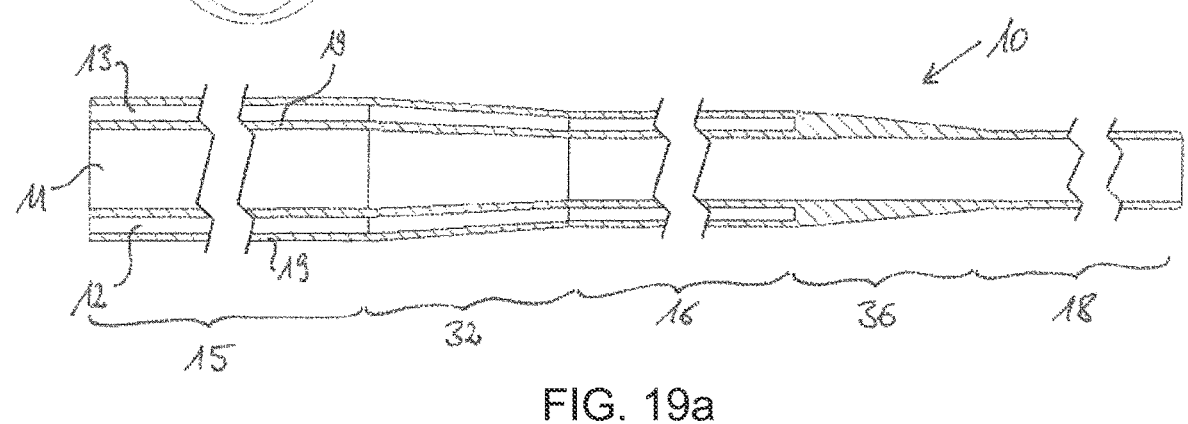

A further alternative exemplary embodiment of an inventive catheter is shown in FIGS. 14 and 15. Catheter tube according to FIGS. 14 and 15 has a proximal catheter portion 15 and a distal catheter portion 16. Proximal catheter portion 15 has a larger outside diameter than distal catheter portion 16. Within distal catheter portion 16, catheter tube 10 supports a heat-exchanger element 14. In the present case, heat-exchanger element 14 is formed as a compliant balloon. In other words, the balloon is elastic, and so it dilates radially under fluid pressure.

According to FIGS. 14 and 15, the temperature-regulating circuit can be seen in the longitudinal section through catheter tube 10. The temperature-regulating circuit comprises first temperature-regulating lumen 12, a distal fluid opening 32 in outer wall 20, heat-exchanger element 14 or the compliant balloon, a proximal fluid opening 34 in outer wall 20 and second temperature-regulating lumen 13.

The balloon or heat-exchanger element 14 is joined fluid-tightly to outer wall 20, so that temperature-regulating fluid can flow from distally to proximally through the balloon, i.e. from distal fluid opening 33 to proximal fluid opening 34. A catheter tip 18, which seals temperature-regulating lumens 12, 13 fluid-tightly, is mounted at the distal axial end of catheter tube 10. Catheter tip 18 has a through hole 27, which is joined to through-lumen 11, so that an instrument, for example a guide wire, may be guided through catheter tube 10 to the point of treatment.

The compliant balloon or heat-exchanger element in rest condition forms a cylindrical tube which, as illustrated in FIG. 14, is disposed within receiving space 17 between proximal outer peripheral level 28 and distal outer peripheral level 29. In the exemplary embodiment according to FIGS. 14 and 15, receiving space 17 is bounded in longitudinal axial direction by transition portion 32 on the one hand and by catheter tip 18 on the other hand. Catheter tip 18 preferably has an outside diameter that corresponds to the outside diameter of proximal catheter portion 15. In this way, the balloon or heat-exchanger element 14, while catheter tube 10 is being advanced through a sheath or through a blood vessel, does not come into contact with either a sheath wall or a vessel wall. Thus no friction develops between a sheath wall or a vessel wall and heat-exchanger element 14, thus facilitating the advancing of catheter tube 10 on the whole. Specifically, it is possible to dispense with a friction-inhibiting or friction-reducing coating of the balloon or heat-exchanger element 14, which otherwise may impair heat transfer via heat-exchanger element 14. In this way heat-exchanger element 14 exhibits improved heat-transfer behavior.

FIG. 15 shows the exemplary embodiment according to FIG. 14, wherein the balloon or heat-exchanger element 14 has assumed the expanded condition. The expanded condition is achieved by the fluid pressure when temperature-regulating fluid, especially a cooling medium, flows through temperature-regulating lumens 12, 13 and heat-exchanger element 14. The fluid pressure causes dilation of the compliant balloon, thus increasing the heat-transfer area. This further increases the efficiency of the inventive catheter as a heat exchanger or for hypothermic treatment.

The inventive catheter may be used in particular for local blood cooling of cerebral blood vessels. Such therapeutic hypothermia may be used in particular for treatment of a stroke. Preferably the catheter is combined with a recanalization element, for example a thrombus trap. During the hypothermic treatment, the recanalization element may be guided through through-lumen 11 to a thrombus, and may then capture and remove the thrombus.

Within the sense of improved bending flexibility with simultaneously high heat-exchange effect and good advancability of the catheter, the invention proposes in general to make the cross-sectional diameter of catheter tube 10 smaller in distal catheter portion 16 than in proximal catheter portion 15. Thereby proximal catheter portion 15 is reinforced, leading to improved pushability during advancing of the catheter. An increased wall thickness in proximal catheter portion 15 also improves the insulating effect of outer wall 20. A smaller wall thickness in distal catheter portion 16 leads to higher flexibility. In general, catheter tube 10 may be subdivided into further sub-regions, wherein catheter geometry, wall thickness, material properties and/or the porosity of outer layer 22 or of outer tube 24 may vary. As regards the dimensions of the catheter, the following values are generally applicable:

For an outside diameter of proximal catheter portion 15 larger than 2 mm, the length of catheter tube 10 is preferably at least 80 cm, especially at least 90 cm, especially at least 100 cm, especially at least 110 cm, especially at least 120 cm. The length of catheter tube 10 is preferably at most 140 cm for an outside diameter of proximal catheter portion 15 larger than 2 mm.

For an outside diameter of proximal catheter portion 16 smaller than 2 mm, the length of catheter tube 10 is preferably at least 80 cm, especially at least 90 cm, especially at least 100 cm, especially at least 110 cm, especially at least 120 cm, especially at least 130 cm, especially at least 140 cm. The length of catheter tube 10 for an outside diameter of proximal catheter portion 15 smaller than 2 mm is preferably at most 160 cm.

The wall thickness of outer tube 24 is preferably between 100 µm and 300 µm, preferably between 150 µm and 250 µm. If outer wall 20 in proximal catheter portion 15 is provided with an outer layer 22, this preferably has a layer thickness between 50 µm and 150 µm, especially between 70 µm and 130 µm, especially between 90 µm and 100 µm.

On the whole, it is appropriate for preferred exemplary embodiments of the invention, especially in the case of a catheter tube formed in one piece, for the difference of the outside diameter between the proximal catheter portion and the distal catheter portion to be between 100 µm and 1000 µm, especially between 200 µm and 800 µm, especially between 300 µm and 700 µm, especially between 400 µm and 600 µm, preferably especially 500 µm. In this connection the respective three-lumen sub-region (containing three lumens) is being considered (not the tip, if this consists of a single lumen).

For good pushability of catheter tube 10, flexible distal catheter portion 16 is preferably limited in length. In particular, distal catheter portion 16 may have a length that amounts to at most 120 mm, especially at most 100 mm, especially at most 80 mm, especially at most 60 mm. Preferably, however, distal catheter portion is longer than 20 mm.

An exemplary embodiment of the invention has the following technical specifications:

Catheter tube 10 is suitable for advancing through a sheath of 8 French size (inside diameter of the sheath approximately 2.8 mm);

The outside diameter of proximal catheter portion 15 is between 2.3 mm and 2.7 mm, preferably between 2.5 mm and 2.7 mm, especially specifically 2.6 mm;

The outside diameter of distal catheter portion 16 is between (without heat-exchanger element/balloon) 1.9 mm and 2.3 mm, preferably between 2.0 mm and 2.2 mm, especially specifically 2.1 mm;

The overall length of catheter tube 10 is between 1.0 m and 1.2 m, preferably 1.1 m;

The length of distal catheter portion 16 is between 40 mm and 120 mm, especially between 60 mm and 100 mm, preferably between 70 mm and 90 mm, especially specifically 80 mm.

FIG. 16*a* shows one longitudinal and two cross sections of an inventive catheter according to a preferred exemplary embodiment. Catheter tube 10 comprises a proximal catheter portion 15 and a distal catheter portion 16, wherein distal catheter portion 16 has a smaller outside diameter than proximal catheter portion 15. The exemplary embodiment according to FIG. 16*a* corresponds substantially to the exemplary embodiment according to FIG. 13. However, in catheter tube 10 according to FIG. 16*a*, distal catheter portion 16 is a scaled version of proximal catheter portion 15. In other words, the cross sections of the two catheter portions 15, 16 are similar to one another in the mathematical or geometric sense. In particular, the ratio between the cross-sectional areas of temperature-regulating lumens 12, 13 and inner wall 19 is identical in proximal catheter portion 15 and in distal catheter portion 16. This is clearly visible in FIG. 16*b* and FIG. 16*c*.

A longitudinal section through a distal catheter portion 16 of a catheter tube 10 is shown in FIG. 17*a*. The longitudinal section does not cut through the longitudinal axis of catheter tube 10, but instead is laterally offset (FIG. 17*b*). Through-lumen 11 is clearly visible. In the illustrated exemplary embodiment, a dilator 35 extends through it. Through-lumen 11 has a constant, invariable cross-sectional diameter. In contrast, the outside diameter of catheter tube 10 is variable. In particular, catheter tube 10 has a catheter tip 18, which directly adjoins distal catheter portion 16. Heat-exchanger elements 14 are disposed in distal catheter portion 16, but for reasons of clarity are not illustrated here. Thus distal catheter portion 16 is defined as that portion close to catheter tip 18 which supports the balloon or the balloons.

Besides eccentrically or laterally disposed through-lumen 11, two temperature-regulating lumens 12, 13 extend in catheter tube 10. Temperature-regulating lumens 12, 13 end upstream from a taper 36, which forms the transition from distal catheter portion 16 to catheter tip 18. The taper narrows toward catheter tip 18 and forms substantially a frustoconical outer contour.

FIG. 17c shows a cross section through catheter tube 10 in distal catheter portion 16. Temperature-regulating lumens 12, 13 resembling pulmonary lobes as well as off-centered through-lumen 11, which has a circular cross section, are clearly visible. The cross-sectional geometry of catheter tube 10 in the region of taper 36 is shown in FIG. 17d. Therein the outer wall 20 of catheter tube 10 has an irregular wall thickness. It is also possible for temperature-regulating lumens 12, 13 to continue into taper 36 and also to narrow (gradually), i.e. temperature-regulating lumens 12, 13 may have a distally decreasing cross-sectional diameter in the region of taper 36. In this respect, temperature-regulating lumens 12, 13 may be visible in certain cross-sectional views of taper 36. Preferably the wall thickness in the region of the prolongation of temperature-regulating lumens 12, 13 disposed in proximal catheter portion 15 is larger than on a diametrically opposite side of through-lumen 11.

FIG. 17e shows a cross section through dilator 35 disposed inside through-lumen 11, especially in the region of a dilator tip 35a. The dilator is provided with a guide lumen 35b, which has a constant cross-sectional diameter substantially over the entire length of dilator 35. The dilator is able to be guided over a guide wire through guide lumen 35b to the point of treatment.

Further sections through the catheter or catheter tube 10 according to FIG. 17a are shown in FIGS. 18a, 18b, 19a, and 19b, wherein a proximal catheter portion 15 is also illustrated. It can be seen that catheter tube 10 has a transition portion 32, which is disposed between proximal catheter portion 15 and distal catheter portion 16. Catheter tip 18 adjoins distal catheter portion 16 via taper 36. Temperature-regulating lumens 12, 13 of catheter tube 10 extend via transition portion 32 into distal catheter portion 16, which supports heat-exchanger elements 14 (not illustrated here). The wall thickness of inner wall 19 and of outer wall 20 may be constant in transition portion 32. Preferably, however, the wall thickness varies in direct proportion to the change of the outside diameter or to the change of the cross-sectional diameter of temperature-regulating lumens 12, 13.

Catheter tip 18 may in general comprise a material that is softer or more flexible than the material of proximal and/or distal catheter portion 15, 16. In this way it is ensured that catheter tip 18 can be guided easily into the desired target vessel in the region of vessel branches, especially bifurcations. Moreover, good contact with a dilator 36 is ensured in this way, which achieves advantages especially for the sheath variant. Finally, catheter tip 18 has advantages for aspiration of thrombi, since the distal opening of through-lumen 11 is located more distally by virtue of catheter tip 18. In this respect it has proved expedient when catheter tip 18 has a length of at least 0.5 cm, especially at least 1 cm, especially at least 2 cm, especially at least 3 cm, especially at least 4 cm, especially at least 5 cm. At most, catheter tip 18 should have a length of 8 cm. In general, it is also provided that catheter tip 18 contains only one single lumen, especially through-lumen 11. Preferably catheter tip 18 has a distally tapering outer contour.

In this connection, it is pointed out that the diagrams according to FIGS. 17a to 19a, 19b may relate both to the sheath variant and to the catheter variant of the catheter. In the sheath variant, the catheter, especially catheter tube 10, may itself assume the function of a sheath, so that an additional sheath for puncturing a blood vessel and for guiding the catheter is not necessary. In the catheter variant, catheter tube 10 is guided to the point of treatment via a sheath introduced beforehand into the blood vessel.

As regards the geometry of catheter tube 10 at its proximal end, the use of a Luer-Lock adapter is provided. The Luer-Lock adapter is preferably joined firmly to catheter tube 10 and it permits access, especially for guide wires and/or fluids, to the various lumens of catheter tube 10. In particular, the Luer-Lock adapter is designed in such a way that, via this, an access to temperature-regulating lumens 12, 13 as well as to through-lumen 11 is possible.

As regards the dimensions of a catheter tube of an inventive catheter (catheter variant), which can be advanced in particular via a sheath of 8 French size, the following characteristic values are preferred:

|  | Proximal catheter portion | Distal catheter portion |
|---|---|---|
| Outside diameter [mm] | 2.3-2.8 advantageously: 2.5-2.7 preferably: | 1.9-2.3 advantageously: 2.0-2.2 preferably: |
| Total length [m] | 0.9-1.3 advantageously: 1.0-1.2 preferably: 1.1 | |
| Length of the distal catheter portion or balloon region [mm] | 40-160 advantageously: 60-140 advantageously: 80-120 advantageously: 90-110 preferably: 100 | |
| Length of the transition region [mm] | at least 10 and at most 120 or at most 100 or at most 80 or at most 60 or at most 40 or at most 30 or at most 20 | |
| Wall thickness [μm] | 100-300 advantageously: 150-250 preferably: 200 | 50-250 advantageously: 100-200 preferably: 150 |
| Ratio of outside diameter of distal catheter portion/ outside diameter of proximal catheter portion | 0.6-0.95 advantageously: 0.7-0.9 preferably: 0.8 | |
| Difference between outside diameter of distal catheter portion and outside diameter of proximal catheter portion | 200-1000 advantageously: 300-800 advantageously: 400-600 preferably: 500 | |

As regards the dimensions of a catheter tube 10 of an inventive catheter (sheath variant), which in the context of a double function acts both as a sheath for an 8 French catheter and also as a catheter, the following characteristic values are preferred:

|  | Proximal sheath portion | Distal sheath portion |
|---|---|---|
| Outside diameter [mm] | 3.2-4.0<br>advantageously: 3.4-3.9<br>advantageously: 3.5-3.8<br>preferably: 3.6-3.7 | 2.3-3.6<br>advantageously: 2.6-3.4<br>advantageously: 2.8-3.3<br>advantageously: 2.9-3.2<br>preferably: 3.0-3.1 |
| Inside diameter of the through-lumen [mm] | | |
| 5F variant | | 1.7-2.1<br>Preferably: 1.8-2.0 |
| 6F variant | | 2.1-2.4<br>Preferably: 2.2-2.3 |
| Total length [m] | | 0.8-1.0<br>preferably: 0.9 |
| Length [mm] | | 40-120<br>advantageously: 60-100<br>advantageously: 70-90<br>preferably: 80 |
| Length of the transition region [mm] | | at least 10<br>and at most 120<br>or at most 100<br>or at most 80<br>or at most 60<br>or at most 40<br>or at most 30<br>or at most 20 |
| Wall thickness [μm] | 100-400<br>advantageously: 200-300<br>preferably: 250 | 50-300<br>advantageously: 150-250<br>preferably: 200 |
| Ratio of outside diameter of distal catheter portion/outside diameter of proximal catheter portion | 0.6-0.95<br>advantageously: 0.7-0.9<br>preferably: 0.8 | |
| Difference between outside diameter of distal catheter portion and outside diameter of proximal catheter portion | | 100-1000<br>advantageously: 200-1000<br>advantageously: 300-800<br>advantageously: 400-600<br>preferably: 500 |

As follows from the tables, within the scope of the present invention we distinguish between a sheath and a catheter when referring to size values. For a catheter, the size value in French relates to the outside diameter of the catheter tube. In contrast, a sheath with the same size value has a larger outside diameter, since the size value of a sheath relates instead to the maximum size of a catheter than can be advanced through the sheath. Thus the outside diameter of an 8 French sheath corresponds instead to the outside diameter of an 8 French catheter plus the wall thickness of the sheath.

In principle, a size of 8 French is preferred for the catheter tube in the present invention, wherein this size value relates, in the case of the catheter variant, to the outside diameter and, in the case of the sheath variant, to the inside diameter of the through-lumen (plus a tolerance, so that an 8 French catheter is able to be pushed through through-lumen 11). Nevertheless, other sizes are also possible. Catheter tube 10 may also be scaled, so that sizes of 4, 6, 5 or 7 French up to 9, 10, 11 or 12 French are attained. In such cases the dimensions of the individual lumens as well as inner and outer walls of catheter tube 10 are preferably at least approximately proportional to one another.

LIST OF REFERENCE SYMBOLS

10 Catheter tube
11 Through-lumen
12 First temperature-regulating lumen
13 Second temperature-regulating lumen
14 Heat-exchanger element
15 Proximal catheter portion
16 Distal catheter portion
17 Receiving space
18 Catheter tip
19 Inner wall
20 Outer wall
21 Inner layer
22 Outer layer
23 Inner tube
24 Outer tube
25 Spacer
26 Insulating space
27 Through opening
28 Proximal outer peripheral level
29 Distal outer peripheral level
30 Proximal closure flange
31 Distal closure flange
32 Transition portion
33 Distal fluid opening
34 Proximal fluid opening
35 Dilator
35*a* Dilator tip
35*b* Guide lumen
36 Taper

The invention claimed is:
1. A medical catheter for hypothermic treatment; the medical catheter comprising:

a catheter tube comprising
arranged in an axial direction of the catheter tube, a proximal catheter portion, a distal catheter portion, and a heat-exchanger element disposed in its entirety at a distal portion of the distal catheter portion,
a first outside diameter in the distal catheter portion and a second outside diameter in the proximal catheter portion, the first outside diameter being smaller than the second outside diameter,
a first bending flexibility at the distal catheter portion and a second bending flexibility at the proximal catheter portion, the first bending flexibility is greater than the second bending flexibility,
a through-lumen, and
at least two temperature-regulating lumens;
the heat-exchanger element in fluid communication with the at least two temperature-regulating lumens; and
a temperature-regulating circuit comprising the heat-exchanger element and the at least two temperature-regulating lumens;
wherein the heat-exchanger element comprises a compressed state,
wherein the heat-exchanger element in the compressed state comprises a cross-sectional diameter equal to or smaller than the second outside diameter of the proximal catheter portion;
wherein the at least two temperature-regulating lumens comprise a first cross-sectional area in the proximal catheter portion and a second cross-sectional area in the distal catheter portion; and
wherein the first cross-sectional area is larger than the second cross-sectional area.

2. The medical catheter of claim 1, further comprising a first wall thickness of the catheter tube in the distal catheter portion and a second wall thickness of the catheter tube in the proximal catheter portion, the first wall thickness being smaller than the second wall thickness.

3. The medical catheter of claim 1, further comprising a receiving space for receiving the heat-exchanger element, the receiving space being formed on the distal catheter portion between a first outer peripheral level of the distal catheter portion and a second outer peripheral level of the proximal catheter portion,
the heat-exchanger element in the compressed state is disposed completely inside the receiving space.

4. The medical catheter of claim 1, wherein the catheter tube comprises a unitary structure.

5. The medical catheter of claim 1, wherein the catheter tube comprises two-layer outer wall in the proximal catheter portion.

6. The medical catheter of claim 5, wherein the outer wall comprises, in the proximal catheter portion, an inner layer and an outer layer or, in the distal catheter portion, the inner layer.

7. The medical catheter of claim 6, wherein the inner layer or the outer layer comprises a porous structure or hollow spheres.

8. The medical catheter of claim 6, wherein the outer layer comprises a thermal conductivity of at most 0.2 $Wm^{-1}K^{-1}$.

9. The medical catheter of claim 1,
wherein the catheter tube comprises an outer tube and an inner tube, the outer tube being larger than the inner tube;
further comprising an insulating space formed between the outer tube and the inner tube.

10. The medical catheter of claim 9, wherein the outer tube and the inner tube being aligned eccentrically relative to one another.

11. The medical catheter of claim 9, further comprising a spacer is disposed between the outer tube and the inner tube proximal to the at least two temperature-regulating lumens.

12. The medical catheter of claim 11, wherein the spacer is formed by shaping the axial end of the outer tube.

13. The medical catheter of claim 9, wherein the outer wall of the catheter tube comprises a wall thickness that is constant.

14. The medical catheter of claim 1,
wherein the catheter tube comprises a catheter tip at a distal axial end of the catheter tube,
the catheter tip comprising a first cross-sectional diameter,
the distal catheter portion comprising a second cross-sectional diameter;
wherein the first cross-sectional diameter is larger than the second cross-sectional diameter.

15. The medical catheter of claim 1, wherein each of the at least two temperature-regulating lumens respectively comprise a cross-sectional profile in a shape of a pulmonary lobe.

16. The medical catheter of claim 1, wherein the through-lumen and the at least two temperature-regulating lumens are separated by an inner wall, the inner wall being flexible to vary respective cross-sectional areas of the at least two temperature-regulating lumens.

17. The medical catheter of claim 1,
further comprising a receiving region for a medical instrument is disposed in the distal catheter portion, the receiving region comprising a first cross-sectional diameter and the through-lumen comprising a second cross-sectional diameter, the first cross-sectional diameter is larger than the second cross-section diameter.

18. The medical catheter of claim 1, wherein the catheter tube comprises a catheter tip, wherein only the through-lumen extends through the catheter tip.

19. A treatment system comprising:
a medical catheter for hypothermic treatment; the medical catheter comprising:
a catheter tube comprising
a proximal catheter portion and a distal catheter portion,
a first outside diameter in the distal catheter portion and a second outside diameter in the proximal catheter portion, the first outside diameter being smaller than the second outside diameter,
a through-lumen, and
at least two temperature-regulating lumens;
a heat-exchanger element disposed in its entirety in the distal catheter portion and being in fluid communication with the at least two temperature-regulating lumens; and
a temperature-regulating circuit comprising a heat-exchanger element and the at least two temperature-regulating lumens; and
a self-expandable device joined to an elongated guide element, the self-expandable device being longitudinally displaceable together with the guide element, the self-expandable device being longitudinally displaceable together with the guide element in the through-lumen;
wherein the heat-exchanger element comprises a compressed state, wherein the heat-exchanger element in the compressed state comprises a cross-sectional diameter equal to or smaller than the second outside diameter of the proximal catheter portion;

wherein the catheter tube comprises a first bending flexibility at the distal catheter portion and a second bending flexibility at the proximal catheter portion, the first bending flexibility is greater than the second bending flexibility;

wherein the at least two temperature-regulating lumens comprise a first cross-sectional area in the proximal catheter portion and a second cross-sectional area in the distal catheter portion; and wherein the first cross-sectional area is larger than the second cross-sectional area.

20. The treatment system of claim 19, further comprising a microcatheter and a guide catheter;

wherein the self-expandable device is disposed displaceably in the microcatheter, the microcatheter being longitudinally displaceably inside the guide catheter.

21. The treatment system of claim 19, further comprising a guide catheter, the guide catheter is longitudinally displaceable in the through-lumen.

22. A method for making a medical catheter, the medical catheter for hypothermic treatment; the medical catheter comprising:

a catheter tube comprising
 a proximal catheter portion and a distal catheter portion,
  a first outside diameter in the distal catheter portion and a second outside diameter in the proximal catheter portion, the first outside diameter being smaller than the second outside diameter,
 a through-lumen, and
 at least two temperature-regulating lumens;
a heat-exchanger element disposed in the distal catheter portion and being in fluid communication with the at least two temperature-regulating lumens; and
a temperature-regulating circuit comprising a heat-exchanger element and the at least two temperature-regulating lumens;

the method comprising the step of:

forming the catheter tube in one piece from a single material or from several different materials by an extrusion process;

wherein the heat-exchanger element comprises a compressed state, wherein the heat-exchanger element in the compressed state comprises a cross-sectional diameter equal to or smaller than the second outside diameter of the proximal catheter portion;

wherein the catheter tube comprises a first bending flexibility at the distal catheter portion and a second bending flexibility at the proximal catheter portion, the first bending flexibility is greater than the second bending flexibility;

wherein the at least two temperature-regulating lumens comprise a first cross-sectional area in the proximal catheter portion and a second cross-sectional area in the distal catheter portion; and wherein the first cross-sectional area is larger than the second cross-sectional area.

\* \* \* \* \*